(12) United States Patent
Rispoli et al.

(10) Patent No.: US 11,693,078 B2
(45) Date of Patent: Jul. 4, 2023

(54) HYBRID SPATIAL AND CIRCUIT OPTIMIZATION FOR TARGETED PERFORMANCE OF MRI COILS

(71) Applicant: Purdue Research Foundation, West Lafayette, IN (US)

(72) Inventors: Joseph V. Rispoli, West Lafayette, IN (US); Xin Li, Saint Anthony, MN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/667,480

(22) Filed: Feb. 8, 2022

(65) Prior Publication Data

US 2022/0260661 A1 Aug. 18, 2022

Related U.S. Application Data

(60) Provisional application No. 63/146,713, filed on Feb. 8, 2021.

(51) Int. Cl.
*G01R 33/565* (2006.01)
*G01R 33/28* (2006.01)
*A61B 5/055* (2006.01)
*G01R 33/3415* (2006.01)
*G01R 33/54* (2006.01)

(52) U.S. Cl.
CPC ......... *G01R 33/5659* (2013.01); *A61B 5/055* (2013.01); *G01R 33/288* (2013.01); *G01R 33/3415* (2013.01); *G01R 33/543* (2013.01)

(58) Field of Classification Search
CPC .............. G01R 33/5659; G01R 33/288; G01R 33/3415; G01R 33/543; A61B 5/055
See application file for complete search history.

(56) References Cited

U.S. PATENT DOCUMENTS 8,652,440 B2 *  2/2014  Ichise ............... A61K 51/0455
                                                     424/9.1
9,841,477 B2    12/2017  Kozlov et al.
10,156,621 B2 * 12/2018  Zhai .................... G01R 33/586
(Continued)

OTHER PUBLICATIONS

Vaughan et al., Whole-body imaging at 7T: preliminary results. Magn Reson Med. 2009;61:244-248.
(Continued)

*Primary Examiner* — Dixomara Vargas
(74) *Attorney, Agent, or Firm* — Piroozi-IP, LLC

(57) ABSTRACT

A method of operating a multi-coil magnetic resonance imaging system, is disclosed which includes establishing initial circuit values of a drive circuit, loading a tissue model associated with a tissue to be imaged, loading target values for a variable of interest (VOI) associated with operation of two or more coils of a magnetic resonance imaging system, performing a simulation based on the established circuit values and the loaded tissue model, determining output values of the VOI based on the simulation, comparing the simulated output values of the VOI to the loaded target values of the VOI, if the simulated output values are outside of a predetermined envelope about the loaded target values of the VOI, then performing a first optimization until the simulated output values are within the predetermined envelope.

20 Claims, 19 Drawing Sheets
(13 of 19 Drawing Sheet(s) Filed in Color)

(56) References Cited

U.S. PATENT DOCUMENTS

| | | | |
|---|---|---|---|
| 10,321,958 B2* | 6/2019 | Taylor | G06T 11/008 |
| 10,527,695 B2* | 1/2020 | Cohen | G01R 33/50 |
| 10,912,476 B2* | 2/2021 | Spector | A61B 5/287 |
| 2012/0153951 A1 | 6/2012 | Kozlov et al. | |
| 2012/0256626 A1* | 10/2012 | Adalsteinsson | G01R 33/5612 324/309 |
| 2013/0271144 A1 | 10/2013 | Avdievich et al. | |
| 2014/0152309 A1 | 6/2014 | Kozlov et al. | |
| 2015/0028869 A1 | 1/2015 | Kozlov et al. | |
| 2015/0268321 A1* | 9/2015 | Zhai | G01R 33/288 324/309 |
| 2016/0155238 A1* | 6/2016 | Bachschmidt | A61B 5/0037 382/131 |
| 2017/0007148 A1* | 1/2017 | Kaditz | A61B 5/055 |
| 2017/0011255 A1* | 1/2017 | Kaditz | G01R 33/48 |
| 2017/0285122 A1* | 10/2017 | Kaditz | G01R 33/445 |
| 2017/0285123 A1* | 10/2017 | Kaditz | G01R 33/5608 |
| 2018/0058211 A1* | 3/2018 | Liang | G01V 1/282 |
| 2018/0211387 A1* | 7/2018 | Wang | A61B 5/02007 |
| 2021/0312626 A1* | 10/2021 | Griswold | G01R 33/5608 |
| 2021/0330993 A1* | 10/2021 | Falkovskiy | G06T 7/0012 |
| 2022/0229136 A1* | 7/2022 | Kannengiesser | G01R 33/50 |

OTHER PUBLICATIONS

Vaughan et al., 7T vs. 4T: RF power, homogeneity, and signal-to-noise comparison in head images. Magn Reson Med. 2001;46:24-30.

Vaughan et al., High frequency volume coils for clinical NMR imaging and spectroscopy. Magn Reson Med. 1994;32:206-218.

Collins et al., SAR and B1 field distributions in a heterogeneous human head model within a birdcage coil. Magn Reson Med. 1998;40:847-856.

Li et al., Toward 7T breast MRI clinical study: safety assessment using simulation of heterogeneous breast models in RF exposure. Magn Reson Med. 2019;81:1307-1321.

Metzger et al. Local B1+ shimming for prostate imaging with transceiver arrays at 7T based on subject-dependent transmit phase measurements Magn Reson Med. 2008;59:396-409.

Collins et al., Calculations of B1 distribution, SNR, and SAR for a surface coil adjacent to an anatomically-accurate human body model. Magn Reson Med. 2001;45:692-699.

Oezerdem et al., 6-channel bow tie antenna transceiver array for cardiac MR at 7.0 tesla. Magn Reson Med. 2016;75:2553-2565.

Hetherington et al., RF shimming for spectroscopic localization in the human brain at 7 T. Magn Reson Med. 2010;63:9-19.

Padormo et al., Parallel transmission for ultrahigh-field imaging. NMR Biomed. 2016;29:1145-1161.

Mao et al., Exploring the limits of RF shimming for high-field MRI of the human head. Magn Reson Med. 2006;56:918-922.

Guérin et al., Comparison of simulated parallel transmit body arrays at 3 T using excitation uniformity, global SAR, local SAR, and power efficiency metrics. Magn Reson Med. 2015;73:1137-1150.

Adriany et al., A geometrically adjustable 16-channel transmit/receive transmission line array for improved RF efficiency and parallel imaging performance at 7 Tesla. Magn Reson Med. 2008;59:590-597.

Kozlov et al., Fast MRI coil analysis based on 3-D electromagnetic and RF circuit co-simulation. J Magn Reson. 2009;200:147-152.

Zhang et al., Field and S-parameter simulation of arbitrary antenna structure with variable lumped elements. In Proceedings of the 17th Annual Meeting of the ISMRM, Honolulu, Hawaii, 2009. p 3040.

Lemdiasov et al., A numerical postprocessing procedure for analyzing radio frequency MRI coils. Concepts Magn Reson Part A. 2011;38A:133-147. 3476.

Beqiri et al.,Comparison between simulated decoupling regimes for specific absorption rate prediction in parallel transmit MRI Magn Reson Med. 2015;74:1423-1434.

Restivo et al., Improving peak local SAR prediction in parallel transmit using in situ S-matrix measurements. Magn Reson Med. 2017;77:2040-2047.

Sadeghi-Tarakameh et al., In vivo human head MRI at 10.5T: a radiofrequency safety study and preliminary imaging results. Magn Reson Med. 2020;84:484-496.

Lu et al., Optimization of a quadrature birdcage coil for functional imaging of squirrel monkey brain at 9.4T. Magn Reson Imaging. Jun. 2021;79:45-51.

Yan et al., Improved traveling-wave efficiency in 7T human MRI using passive local loop and dipole arrays. Magn Reson Imaging. 2017;39:103-109.

Yan et al., New resonator geometries for ICE decoupling of loop arrays. J Magn Reson. Apr. 2017;277:59-67.

Yan et al., Optimizing the ICE decoupling element distance to improve monopole antenna arrays for 7 Tesla MRI. Magn Reson Imaging. Nov. 2016;34(9):1264-1268.

Yan et al., Simulation verification of SNR and parallel imaging improvements by ICE-decoupled loop array in MRI. Appl Magn Reson. Apr. 2016;47(4):395-403.

Yan et al., Theoretical analysis of magnetic wall decoupling method for radiative antenna arrays in ultrahigh magnetic field MRI. Concepts Magn. Reson. 2015; 45: 183-190.

Yan et al., Multichannel Double-Row Transmission Line Array for Human MR Imaging at Ultrahigh Fields. IEEE Trans Biomed Eng. Jun. 2015;62(6):1652-9.

Yan et al., Optimization of an 8-Channel Loop-Array Coil for a 7 T MRI System with the Guidance of a Co-Simulation Approach. Appl Magn Reson 2014 45, 437-449.

Yan et al., 7T transmit/receive arrays using ICE decoupling for human head MR imaging. IEEE Trans Med Imaging. Sep. 2014;33(9):1781-7.

Yan et al., Tuning Microstrip Coil Field Patterns Using Capacitor-Segmented Ground Planes, Proceedings of 24th ISMRM meeting, 2016, 3533.

Avdievich et al., Analytical modeling provides new insight into complex mutual coupling between surface loops at ultrahigh fields. NMR in Biomedicine. 2017; 30:e3759.

Avdievich et al., Combination of surface and 'vertical' loop elements improves receive performance of a human head transceiver array at 9.4 T. NMR in Biomedicine. 2018; 31:e3878.

Avdievich et al., Evaluation of transmit efficiency and SAR for a tight fit transceiver human head phased array at 9.4 T. NMR in Biomedicine. 2017; 30:e3680.

Avdievich et al., Novel splittable N-Tx/2N-Rx transceiver phased array to optimize both signal-to-noise ratio and transmit efficiency at 9.4T. Magn. Reson. Med. 2016; 76: 1621-1628.

Collins et al., Calculation of radiofrequency electromagnetic fields and their effects in MRI of human subjects. Magn. Reson. Med. 2011; 65: 1470-1482.

Avdievich et al., Improved homogeneity of the transmit field by simultaneous transmission with phased array and volume coil. J. Magn. Reson. Imaging, 2010; 32: 476-481.

Giannakopoulos et al., "Global Maxwell Tomography using an 8-channel radiofrequency coil: simulation results for a tissue-mimicking phantom at 7T," 2019 IEEE International Symposium on Antennas and Propagation and USNC-URSI Radio Science Meeting, 2019, pp. 823-824.

Lattanzi et al., Approaching ultimate intrinsic signal-to-noise ratio with loop and dipole antennas. Magn Reson Med. Mar. 2018;79(3):1789-1803.

Zhang et al., Whole body traveling wave magnetic resonance imaging at high field strength: Homogeneity, efficiency, and energy deposition as compared with traditional excitation mechanisms. Magn. Reson. Med. 2012; 67: 1183-1193.

Shajan et al., A 16-channel dual-row transmit array in combination with a 31-element receive array for human brain imaging at 9.4 T. Magn Reson Med. 2013;71:870-879.

Li et al., ICE decoupling technique for RF coil array designs. Med Phys. 2011;38:4086-4093.

Avdievich et al., Resonant inductive decoupling (RID) for transceiver arrays to compensate for both reactive and resistive components of the mutual impedance. NMR Biomed. 2013;26:1547-1554.

(56) References Cited

OTHER PUBLICATIONS

Yan et al., Self-decoupled radiofrequency coils for magnetic resonance imaging. Nat Commun. 2018;9:3481.

Adriany et al., Evaluation of a 16-channel transmitter for head imaging at 10.5T. In: Proceedings of the 21st International Conference on Electromagnetics in Advanced Applications, Granada, Spain, 2019. pp 1171-1174.

Hoffmann et al., Numerical and experimental evaluation of RF shimming in the human brain at 9.4 T using a dual-row transmit array. Magn Reson Mater Physics Biol Med. 2014;27:373-386.

Avdievich et al., Double-tuned 31P/1H human head array with high performance at both frequencies for spectroscopic imaging at 9.4T. Magn Reson Med. 2020;84:1076-1089.

Avdievich et al., Improved longitudinal coverage for human brain at 7T: a 16 element transceiver array. In: Proceedings of the 19th Annual Meeting of the ISMRM, Montreal, Québec, Canada, 2011. p. 328.

Avdievich, Transceiver-phased arrays for human brain studies at 7 T. Appl Magn Reson. 2011;41:483-506.

Nagaoka et al., Development of realistic high-resolution whole-body voxel models of Japanese adult males and females of average height and weight, and application of models to radio-frequency electromagnetic-field dosimetry. Phys Med Biol. 2004;49:1-15.

Christ et al., The virtual family—development of surface-based anatomical models of two adults and two children for dosimetric simulations. Phys Med Biol. 2010;55:N23-N38.

Gosselin et al., Development of a new generation of high-resolution anatomical models for medical device evaluation: the virtual population 3.0. Phys Med Biol. 2014;59:5287-5303.

Kozlov et al., Investigation of the decoupling between MRI array elements. In: Proceedings of the 43rd European Microwave Conference, Nuremberg, Germany, 2013 pp. 1223-1226.

Le Garrec et al., Probabilistic analysis of the specific absorption rate intersubject variability safety factor in parallel transmission MRI Magn Reson Med. 2016;78:1217-1223.

De Greef et al., Specific absorption rate intersubject variability in 7T parallel transmit MRI of the head. Magn Reson Med. 2012;69:1476-1485.

Hoffmann et al., Safety testing and operational procedures for self-developed radiofrequency coils. NMR Biomed., 29, 2015: 1131-1144.

Ertürk et al., Toward imaging the body at 10.5 tesla. Magn. Reson. Med. 2017,77: 434-443.

Ertürk et al., A 16-channel combined loop-dipole transceiver array for 7 Tesla body MRI. Magn. Reson. Med. 2017,77: 884-894.

Lu et al., Optimization of a transmit/receive surface coil for squirrel monkey spinal cord imaging. Magn Reson Imaging. May 2020;68:197-202.

* cited by examiner

HYBRID SPATIAL AND CIRCUIT OPTIMIZATION FOR TARGETED PERFORMANCE OF MRI COILS

CROSS-REFERENCE TO RELATED APPLICATIONS

This application is related to and claims the priority benefit of U.S. Provisional Patent Application having Ser. No. 63/146,713 titled "Hybrid Spatial and Circuit Optimization for Targeted Performance of MRI Coils" which was filed Feb. 8, 2021, the contents of which are hereby incorporated by reference in its entirety into the present disclosure.

STATEMENT REGARDING GOVERNMENT FUNDING

This invention was made with government support under contract numbers EB011639, EB024408, EB026231 and NS090417 awarded by the National Institutes of Health. The government has certain rights in the invention.

TECHNICAL FIELD

The present disclosure generally relates to magnetic resonance imaging (MRI) systems, and in particular, to an MRI system with a multi-channel transmit coil and a method of optimization of performance of same.

BACKGROUND

This section introduces aspects that may help facilitate a better understanding of the disclosure. Accordingly, these statements are to be read in this light and are not to be understood as admissions about what is or is not prior art.

Magnetic Resonance Imaging (MRI) has been a hallmark of imaging biological tissues (e.g., a human brain) for decades, and has been utilized ubiquitously. Reference is made to U.S. Pat. Pub. 2015/0028869 in which a list of references are cited (U.S. Pat. Nos. 7,573,270; 7,501,823; 7,358,923; 7,358,923; 7,345,485; 7,298,145; 7,285,957; 7,173,425; 7,088,104; 7,088,100; 7,012,429; 6,940,466; 6,853,193; 6,771,070; 6,552,544; 6,538,442; 6,107,798; 6,011,395; 5,998,999; 5,791,648; 5,642,048; 5,610,521; 5,565,779; 5,483,163; 5,483,158; 5,473,252; 5,461,314; 5,365,173; 5,243,286; 5,196,797; 5,185,575; 5,172,061; 5,159,929; 5,081,418; 4,926,125; 4,918,388; 4,885,539; 4,879,516; 4,871,969; 4,820,985; 4,788,503; 4,783,641; 4,780,677; 4,752,736; 4,751,464; 4,737,718; 4,731,584; 4,725,780; 4,721,915; 4,129,822; 4,320,342; and 4,638,253), each of which is incorporated by reference in its entirety into the present disclosure. Further reference is made to U.S. Pat. Pubs. 2012/0153951 and 20140152309, each of which is also incorporated by reference in its entirety into the present disclosure.

As a general proposition, it is critically important to provide high level of coil performance. Coil performance is measured by the how much RF magnetic field is delivered to the coil per unit power. This variable is also measured against RF field homogeneity, without which fast and reliable MR images are difficult to obtain. Nowadays, MRI systems use multi-channel transmission coils (e.g. 16 channels). Coil excitation can occur by a single power source that is then split into a several channels, or alternatively each channel is powered separately by an associated unit. One challenge with such multi-channel transmission coils is EM coupling. It is well known to characterize this electromagnetic coupling by an S-parameter used to denote scattering. Generally, the S-parameter refers to how a network of circuit elements making up a transmit coil system would respond to differing inputs. For example the S-parameter may represent response of the coil system to one frequency input vs. another frequency input. It is important to understand the S-parameter is a complex number with associated magnitude and phase.

In order to overcome the electromagnetic coupling challenge, there have been efforts to compensate for the coupling. No matter how the electromagnetic coupling is compensated, it is important that to make the compensation independent of coil loading.

Another challenge is the decreased magnetic field component ($B_1^+$) homogeneity over one or more region of interest (ROI). In order to achieve better homogeneity, RF shimming is a common technique, where amplitude and phase of excitation signals are adjusted for a given ROI, when using a multi-channel transmitter [e.g., see W Gilbert, K M., A T. Curtis, J S. Gati, L M. Klassen, and R S. Menon: "A radiofrequency coil to facilitate $B_1^+$ shimming and parallel imaging acceleration in three dimensions at 7 T," NMR Biomed, vol 24., pp 815-823, 2011.].

Recent regulatory clearance for clinical use of 7 Tesla MRI (7T MRI) has led to increased interest in clinical ultra-high field (UHF) applications. However, to robustly achieve the expected increase in signal to noise ratio associated with UHF MRI systems, the RF challenges need to be met, namely, problems with higher RF power, worse $B_1^+$ homogeneity, and increased tissue conductivity but decreased permittivity at higher frequency, all of which usually results in increased specific absorption rate (SAR). The use of parallel transmission (pTx) coils combined with techniques such as RF shimming and parallel excitation can mitigate the effects of $B_1^+$ spatial homogeneity. In particular, RF shimming can provide improvement in $B_1^+$ efficiency while reducing peak local SAR. In the development of such pTx coils, the need for accurate EM simulations for RF safety and performance design is evident. Over the past several years, the state-of-the-art for design and simulation of such coil arrays has advanced via circuit-domain co-simulation strategy to use the S-parameters from a single electromagnetic simulation with RF circuit analysis for coil tuning and matching thereby saving significant time. More specifically, prior art work has described calculation of a closed-form S-parameter matrix to accomplish these simulations. These methods have been used to improve the prediction of local SAR in pTx coils at 3 T, 7 T, and 10.5 T.

As mentioned above, a characteristic challenge to using pTx array is strong interactions between coils, which are not mitigated by preamplifiers as in receive arrays. The strong interactions between coils and the subject at high frequency also make achieving reliable decoupling between elements difficult. In order to minimize these couplings, several approaches have been proposed including capacitive decoupling, inductive decoupling, and other methods such as induced current elimination (ICE), resonant inductive decoupling (RID), and dipole-loop decoupling. These methods range from geometric overlap to additional secondary resonant circuits that can minimize both real and imaginary terms in the impedance matrix. It is clear however that independent of the specific methodology of decoupling, given the decoupling circuit's effect on power distribution, it is important to include its impact in the EM simulation and circuit analysis. However, with the simulation tools available, solutions that include the decoupling circuits are rare.

The dual-row head coil modeled by Adriany and Hoffmann included transformer decoupling (TD) circuits modeled using the built-in toolbox offered in CST MICROWAVE STUDIO 2018. However, more complex features, such as the Q factor and isolated resonant frequency of the TD circuits, are not well modeled and optimized in the EM simulation or circuit analysis software.

Therefore, there remains an unmet need for methods that can assist in the design and optimization of a decoupled transceiver array in MRI systems.

SUMMARY

A method of operating a multi-coil magnetic resonance imaging system is disclosed. The method includes establishing initial circuit values of a drive circuit, loading a tissue model associated with a tissue to be imaged, loading target values for a variable of interest (VOI) associated with operation of two or more coils of a magnetic resonance imaging system, performing a simulation based on the established circuit values and the loaded tissue model, determining output values of the VOI based on the simulation, comparing the simulated output values of the VOI to the loaded target values of the VOI, if the simulated output values are outside of a predetermined envelope about the loaded target values of the VOI, then performing a first optimization. The first optimization includes establishing a cost function based on the VOI, and iteratively minimizing the cost function by iteratively adjusting the circuit values until the cost function changes between iterations is less than a predetermined threshold, re-simulating, and re-comparing the simulated output values of the VOI to the loaded target values of the VOI until the simulated output values are within the predetermined envelope.

A drive system for a multi-coil magnetic resonance imaging system is also disclosed. The system includes two or more coils utilized for imaging a tissue of interest, a drive circuit for driving the two or more coils, a controller having a processor and software loaded on tangible memory adapted to perform: establish initial circuit values of a drive circuit, load a tissue model associated with a tissue to be imaged, load target values for a variable of interest (VOI) associated with operation of two or more coils of a magnetic resonance imaging system, perform a simulation based on the established circuit values and the loaded tissue model, determine output values of the VOI based on the simulation, compare the simulated output values of the VOI to the loaded target values of the VOI, if the simulated output values are outside of a predetermined envelope about the loaded target values of the VOI, then perform a first optimization. The initial optimization includes establish a cost function based on the VOI, and iteratively adjust the cost function by iteratively adjusting the circuit values until the cost function changes between iterations is less than a predetermined threshold, re-simulating, and re-compare the simulated output values of the VOI to the loaded target values of the VOI until the simulated output values are within the predetermined envelope.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
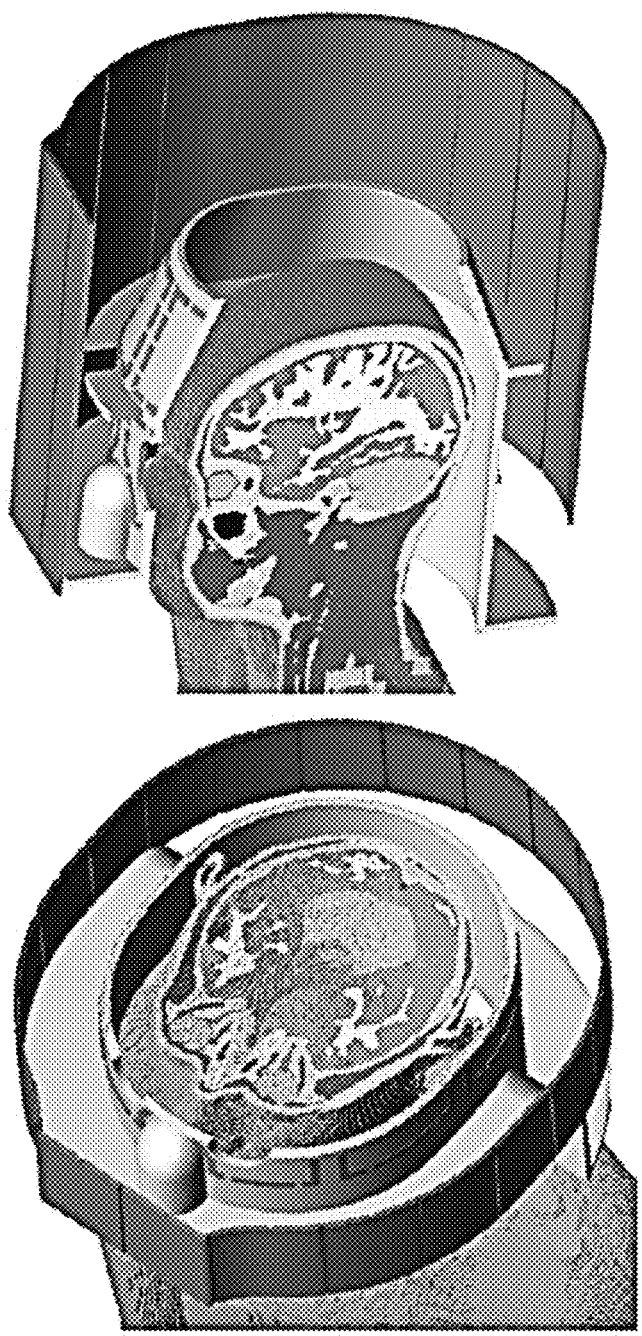
FIG. 1A is a schematic of an magnetic resonance imaging (MRI) system for imaging brain tissue depicting a slotted RF shield.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

A novel method is disclosed herein that can assist in the design and optimization of a decoupled transceiver array in magnetic resonance imaging (MRI) systems. Towards this end, the present disclosure introduces a closed-form S-parameter matrix of a transceiver that accounts for the matching circuits, decoupling circuits, and lumped capacitors. Additionally, a hybrid circuit-spatial domain analysis is introduced that uses a target cost function which includes both the S-parameters and $B_1^+$ homogeneity to determine coil parameters, including capacitors, inductors, and decoupling circuits' Q factors, isolated frequencies, and coupling coefficients. Over a series of four simulated head models and an input range of coil parameters determined from experimental data, this hybrid circuit-spatial domain analysis obtains excellent inter-subject consistency and agreement of actual components. Finally, using the applied amplifier voltages from the MRI console, we generate $B_1^+$ profiles from individual coils which show good agreement with the in vivo data.

To achieve these novel features, the present disclosure presents a closed-form equation of the coil S-parameters and overall spatial $B_1^+$ field, then introduce a cost function associated with the coil S-parameters and the $B_1^+$ homogeneity in a subject's tissue (e.g., the brain tissue), and then minimizing the cost function by optimizing transceiver components, including matching, decoupling circuits, and lumped capacitors. Thereafter, the present disclosure provides a comparison in silico results determined with and without $B_1^+$ homogeneity weighting. Using the known voltage range from the host console, the present disclosure thereafter reconstructs the $B_1^+$ maps of the array coil and provides an RF shimming with four realistic head models. As performed with $B_1^+$ homogeneity weighting, the optimized coil circuit components were highly consistent over the four heads, producing well-tuned, matched, and decoupled coils. The mean peak forward powers and $B_1^+$ statistics in the head models are consistent with in vivo human results (n=8). There are systematic differences in the transceiver components as optimized with or without $B_1^+$ homogeneity weighting, resulting in an improvement of 28.4±7.5% in $B_1^+$ homogeneity with a small 1.9±1.5% decline in power efficiency. Consequently, the co-simulation methodology presented herein accurately simulates the transceiver, predicting consistent S-parameters, component values and $B_1^+$ field. RF shimming of the calculated field maps match with in vivo performance An example MRI system with a double row array coil was modeled in XFdtd (v7.7, REMCOM, STATE COLLEGE, Pa.)—however, it should be understood that other FDTD software can also be used, in 1-mm nominal cell resolution as shown in FIG. 1A, which is a schematic of an MRI system for imaging brain tissue. FIG. 1A, depicts a slotted RF shield that is placed outside the array. The dual-row coil array is made with a former and covered with copper clad board. The simulated human models are positioned in the array center, with the eyes aligned with the eye portals on the array former, mimicking the real scanning scenario. A cylindrical RF shield was used which is made by two layers of overlapped slotted copper foil that are insulated from each other using a thin liquid crystal polymer layer with a relative permittivity of $\varepsilon_r=2$. The slotted copper foil produces a high-pass structure and provides effective RF shielding. The coil former is modeled as polycarbonate ($\varepsilon_r=3$), and the board material of the coil is Bakelite ($\varepsilon_r=3.5$). The volume enclosed by the RF shield is meshed with 1-mm resolution gridding; the rest of the space (including the human body and simulation paddings) are meshed with gridding resolution of at least 20 cells per wavelength. A Japanese head model HANAKO (2-mm resolution adult female), two Virtual Family models ELLA (v1.3 1-mm resolution 26 year old female) and DUKE (v1.3 1-mm resolution 34 year old male), and the Virtual Population model LOUIS (v1.3 1-mm resolution 14 year old male) were loaded separately in the coil center, with coil-to-tissue distance greater than 1 cm. A broadband excitation with convergence criterion of −50 dB resulted a simulation time of 14 minutes per voltage port of a multi-port simulation, running on an Intel Xeon workstation with 64 GB RAM and two QUADRO K5200 GPUs.

Figure 1B:
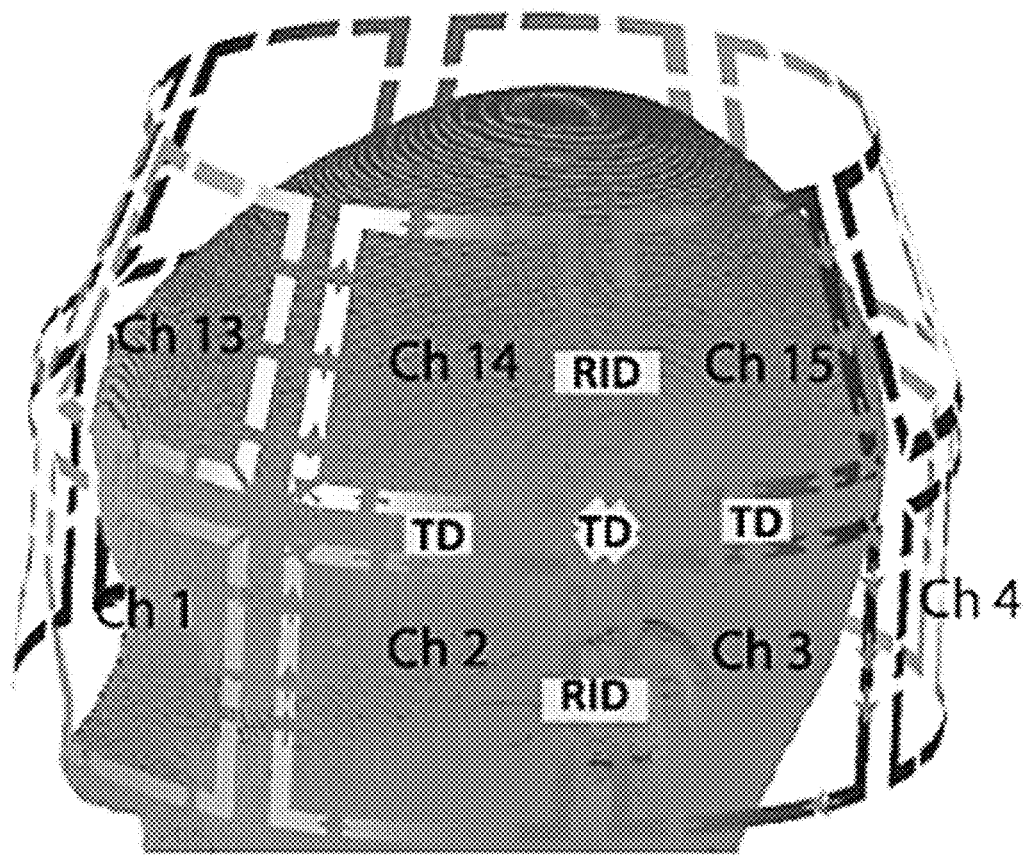
FIG. 1B is a schematic of voltage feeds' orientations of top and bottom row loop coil elements in an FDTD (e.g., XFdtd) setup for a C208×208 S-parameters calculation with arrows showing current direction, with each voltage feed set to 1 V, 50Ω with modulated Gaussian wave excitations.

The array coil (see FIG. 1A) has 208 gaps distributed along the loops and is described by 296 parameters (a listing is shown in Table 1, first column). The voltage feeds are bridged across the gaps in the orientation as shown in FIG. 1B, which is a schematic of voltage feeds' orientations in the XFdtd setup for a $\mathbb{C}$ 208×208 S-parameters calculation with arrows showing current direction, with each voltage feed set to 1 V, 50Ω with modulated Gaussian wave excitations. In the circuit-domain, this array can be modeled as a network of 208 ports, with 16 ports connected to the matching circuits, and 192 ports connected to 112 lumped capacitors and 40 decoupling circuits (using 2 ports each). At a given frequency, the $\mathbb{C}^{208 \times 208}$ S-matrix is $$S_{CoilPorts} = \begin{bmatrix} S_{drive\,drive} & S_{drive\,lump} \\ S_{lump\,drive} & S_{lump\,lump} \end{bmatrix}, \quad [1]$$

where the basic overall system equation is provided below in [4], below, describing the forward wave and reflected wave with the forward wave being defined in [2], below, and the reflected wave being defined in [3], below, wherein $a_{drive}$ and $b_{drive}$ are column vectors that contain 16 complex elements, annotated with complex vector space $\mathbb{C}^{16}$. Specifically, $a_{drive}$ and $b_{drive}$ represent the forward and reflected waves connected to the driving ports on the coils, respectively, $a_{lump}$ and $b_{lump}$ are of $\mathbb{C}^{192}$, representing the forward and reflected waves to the lumped capacitors and decoupling circuits ports.

Figure 1C:
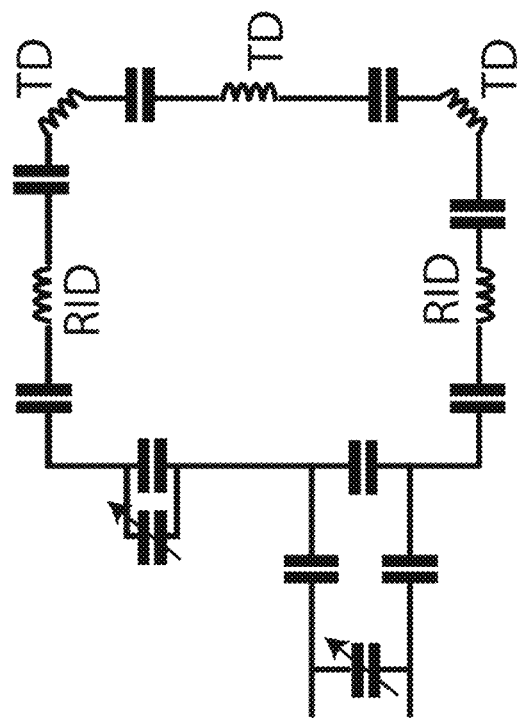
FIG. 1C provides schematics of top and bottom row loop coil elements of FIG. 1B.
Figure 1C:
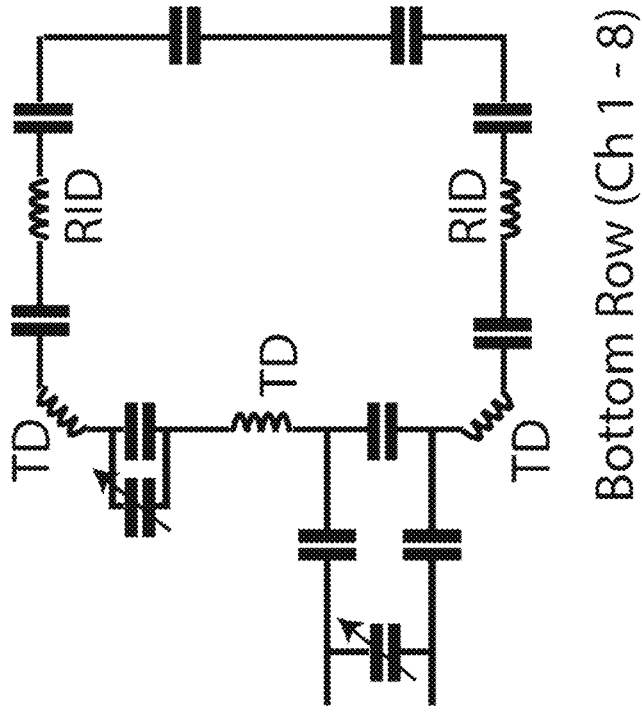
Figure 1D:
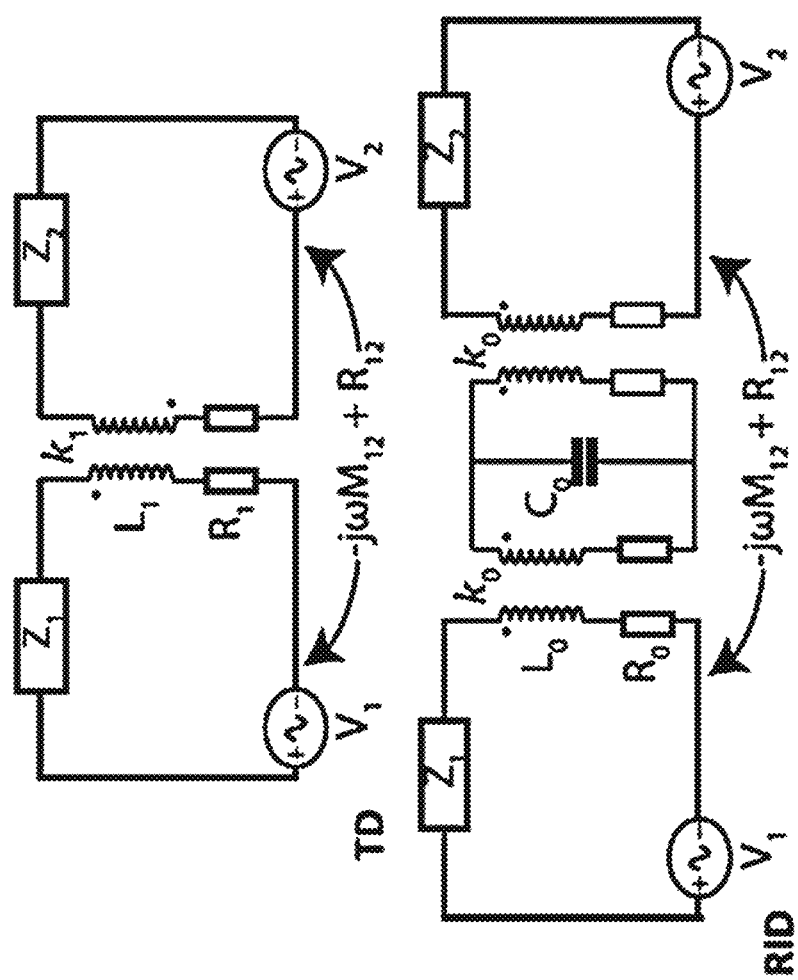
FIG. 1D provides schematics of Resonant inductive decoupling (RID) and transformer decoupling (TD) circuits.

Referring to FIG. 1C, schematics of the top and bottom row loop coil elements are provided. Referring to FIG. 1D, schematics of Resonant inductive decoupling (RID) and transformer decoupling (TD) circuits are provided. In total, 16 RID circuits are applied to decouple neighboring coil elements in the horizontal direction, 8 vertical TD circuits are applied to decouple neighboring elements in the vertical direction, and 16 diagonal TD circuits are applied to decouple neighboring elements in the diagonal direction.

Figure 2:
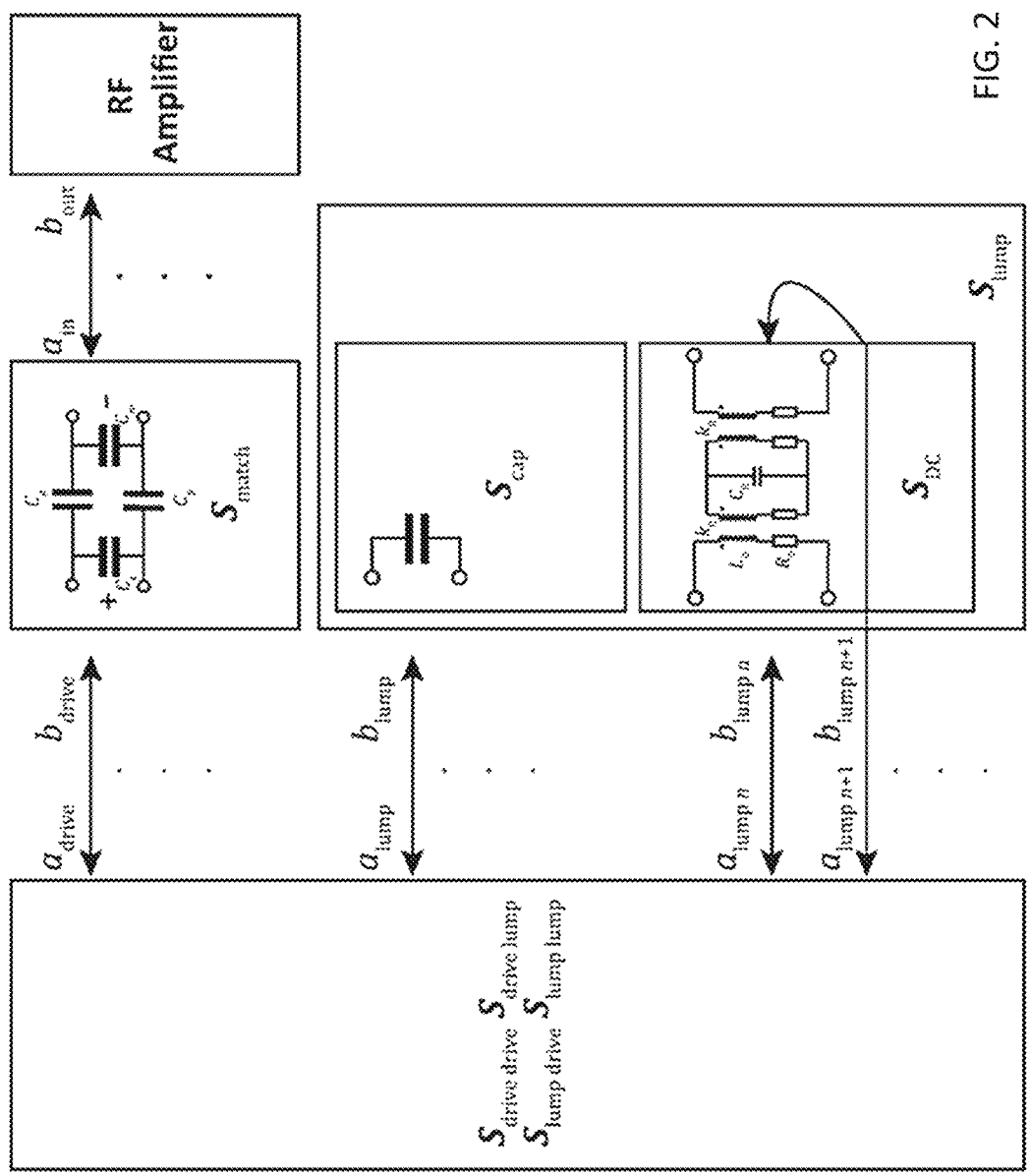
FIG. 2 is a schematic of a 208-port array representing a network system, showing how 8 forward waves from the RF amplifiers are split to 16 forward waves by the splitter, to feed the 16 matching circuits that are connected to the array elements.

With the experimental values for forward and reflected voltages being measured at the amplifier, in this analysis the S-parameters are described at the RF amplifiers, as shown in FIG. 2, defined as $b_{out}/a_{in}$ where $a_{in}$ and $b_{out}$ are the complex forward and reflected voltages, respectively, between the matching circuits and amplifiers. FIG. 2 is a schematic of a 208-port array representing a network system, showing how 8 forward waves from the RF amplifiers are split to 16 forward waves by the splitter, to feed the 16 matching circuits that are connected to the array elements. The array elements are also connected with lumped capacitors and transformer decoupling circuits. Here we show the analysis relating the coil elements used in the optimization to the S-parameters $b_{out}/a_{in}$.

The forward wave to the network system is a column vector expressed by:

$$a = [a_1\ a_2\ \ldots\ a_{208}]^T = [a_{drive}{}^T\ a_{lump}{}^T], \qquad [2]$$

and the reflected waves of the network system are represented by a column vector:

$$b = [b_1\ b_2\ \ldots\ b_{208}]^T = [b_{drive}{}^T\ b_{lump}{}^T]. \qquad [3]$$

The overall relationship of all ports is:

$$\begin{bmatrix} S_{drive\,drive} & S_{drive\,lump} \\ S_{lump\,drive} & S_{lump\,lump} \end{bmatrix} \begin{bmatrix} a_{drive} \\ a_{lump} \end{bmatrix} = \begin{bmatrix} b_{drive} \\ b_{lump} \end{bmatrix}. \qquad [4]$$

from the loop coil toward the matching circuit. In Eq. 5, $S_{lump}$ contains the S matrices of lumped capacitors ($S_{cap}$) and decoupling circuits ($S_{DC}$) described below:

$$S_{lump} = \begin{bmatrix} S_{cap} & 0 \\ 0 & S_{DC} \end{bmatrix} \qquad [6]$$

Next, the S matrices for matching circuits ($S_{match+}$, $S_{match+-}$ and $S_{match-}$), lumped capacitors ($S_{cap}$) and decoupling circuits ($S_{DC}$) are described. The Z matrix for a given matching circuit is written as (using the capacitor notation in FIG. 2):

[6_1]

$$Z_{match} = \begin{bmatrix} S_{match+} & S_{match+-} \\ S_{match+-} & S_{match-} \end{bmatrix} =$$

TABLE 1

Mean ± SD of key components of the 296 optimized parameters (parameter numberings are not in ascending order)

| Components | Hanako | Hanako (exclude $B_1^+$ homogeneity) | Ella | Duke | Louis |
|---|---|---|---|---|---|
| $x_1$-$x_{96}$ Fixed lumped caps (10 pF or 8.2 pF) optimization subject to $x_{1-96} \in$ [7, 13 pF] | 9.66 ± 1.24 | 9.52 ± 0.87 | 9.66 ± 0.91 | 9.53 ± 0.85 | 9.69 ± 0.87 |
| $x_{105}$-$x_{112}$ Tuning cap, top coils [10, 20 pF] | 14.19 ± 0.85 | 13.75 ± 0.50 | 14.80 ± 0.24 | 14.19 ± 0.40 | 14.37 ± 0.56 |
| $x_{97}$-$x_{104}$ Tuning cap, bottom coils [10, 20 pF] | 15.70 ± 1.53 | 15.11 ± 0.45 | 15.43 ± 0.39 | 15.52 ± 0.71 | 15.03 ± 0.55 |
| $x_{121}$-$x_{128}$ Trimmer cap, matching, top coils [5, 20 pF] | 5.56 ± 0.30 | 7.28 ± 0.70 | 6.58 ± 1.01 | 6.61 ± 1.05 | 6.02 ± 0.46 |
| $x_{113}$-$x_{120}$ Trimmer cap, matching, bottom coils [5, 20 pF] | 10.84 ± 2.33 | 7.82 ± 0.51 | 8.39 ± 2.21 | 6.97 ± 1.08 | 7.72 ± 1.29 |
| $x_{129}$-$x_{144}$ Shunt matching cap [5, 20 pF] | 6.22 ± 0.82 | 6.53 ± 0.56 | 6.38 ± 0.79 | 5.92 ± 0.43 | 6.18 ± 0.47 |
| $x_{145}$-$x_{160}$ Parallel matching cap [5, 25 pF] | 18.93 ± 4.08 | 19.55 ± 0.58 | 19.93 ± 2.24 | 20.16 ± 2.69 | 20.14 ± 2.34 |
| $x_{161}$-$x_{168}$ RID inductor, top coils [5, 15 nH] | 9.91 ± 1.05 | 9.34 ± 1.42 | 9.37 ± 0.90 | 10.00 ± 1.46 | 9.55 ± 1.42 |
| $x_{169}$-$x_{176}$ RID inductor, bottom coils [5, 15 nH] | 11.50 ± 1.20 | 9.49 ± 1.49 | 10.31 ± 1.06 | 11.35 ± 1.30 | 10.18 ± 1.63 |
| $x_{201}$-$x_{216}$ RID isolated frequency [200, 298 MHz] | 290.27 ± 2.02 | 292.64 ± 0.87 | 291.48 ± 1.02 | 290.44 ± 1.64 | 291.46 ± 1.72 |
| $x_{241}$-$x_{256}$ RID Q factors [150, 350] | 235.46 ± 22.06 | 216.98 ± 15.90 | 238.24 ± 9.23 | 245.25 ± 16.26 | 236.94 ± 17.22 |
| $x_{281}$-$x_{296}$ RID k coefficients [0.06, 0.5] | 0.282 ± 0.029 | 0.257 ± 0.019 | 0.279 ± 0.014 | 0.295 ± 0.021 | 0.280 ± 0.024 |
| $x_{177}$-$x_{184}$ TD vertical inductors [5, 20 nH] | 17.93 ± 0.49 | 18.47 ± 0.33 | 17.81 ± 0.26 | 17.93 ± 0.29 | 17.79 ± 0.32 |
| $x_{185}$-$x_{200}$ TD diagonal inductors [5, 20 nH] | 8.29 ± 1.38 | 9.98 ± 0.78 | 8.77 ± 1.53 | 9.77 ± 2.99 | 8.97 ± 1.72 |
| $x_{217}$-$x_{240}$ TD Q factors [150, 350] | 249.95 ± 3.32 | 247.76 ± 1.59 | 249.02 ± 1.88 | 250.02 ± 1.42 | 248.92 ± 1.97 |
| $x_{257}$-$x_{264}$ TD vertical k coefficients [0.06, 0.5] | 0.424 ± 0.017 | 0.441 ± 0.014 | 0.435 ± 0.012 | 0.416 ± 0.016 | 0.433 ± 0.014 |
| $x_{265}$-$x_{280}$ TD diagonal k coefficients [0.06, 0.5] | 0.243 ± 0.018 | 0.255 ± 0.013 | 0.256 ± 0.011 | 0.259 ± 0.023 | 0.255 ± 0.016 |

Note:
The square brackets indicate the minimum and maximum values for each parameter. The fixed lumped capacitors are either 10 pF or 8.2 pF capacitors on the actual coils.

The reflected waves can be represented by a function of reflection coefficients and forward waves as described by Lemdiasov (see Lemdiasov R A, Obi A A, Ludwig R. A numerical postprocessing procedure for analyzing radio frequency MRI coils. Concepts Magn Reson Part A 2011). Eq. 5 relates the reflected waves in relation to both the coil array and the matching circuits, as provided below:

$$\begin{bmatrix} b_{drive} \\ b_{lump} \end{bmatrix} = \begin{bmatrix} S_{match+}^{-1} \cdot a_{drive} \\ S_{lump}^{-1} \cdot a_{lump} \end{bmatrix} - \begin{bmatrix} S_{match+-} \cdot S_{match+}^{-1} \cdot a_{in} \\ 0 \end{bmatrix}. \qquad [5]$$

The $S_{match+}$ and $S_{match+-}$ are diagonal matrices for the 16 matching circuits: the diagonal terms are the reflection and the transmission coefficients respectively, when looking -continued $$\begin{bmatrix} \dfrac{-j}{\omega C_s} + \dfrac{j}{\dfrac{C_s C_s}{2\omega} + \dfrac{\omega}{C_p} + \dfrac{\omega}{C_s} + \dfrac{\omega}{C_m}} & -\dfrac{j}{\dfrac{C_m C_s}{2\omega} + \dfrac{\omega}{C_p} + \dfrac{\omega}{C_s} + \dfrac{\omega}{C_m}} \\ -\dfrac{j}{\dfrac{C_m C_s}{2\omega} + \dfrac{\omega}{C_p} + \dfrac{\omega}{C_s} + \dfrac{\omega}{C_m}} & \dfrac{-j}{\omega C_m} + \dfrac{j}{\dfrac{C_m C_m}{2\omega} + \dfrac{\omega}{C_p} + \dfrac{\omega}{C_s} + \dfrac{\omega}{C_m}} \end{bmatrix}.$$

The $S_{match+}$ and $S_{match+-}$ are diagonal matrices for the 16 matching circuits: the reflection coefficient between the coil and matching circuit, and the transmit coefficient between the coil and voltage feeds respectively. $S_{match-}$ is the reflection coefficient between the voltage feed (RF amplifier) and matching circuit. Thus, for the 16 matching circuits:

$$S_{match+} = \begin{bmatrix} S_{1\,match+} & \ddots & 0 \\ \ddots & S_{n\,match+} & \ddots \\ 0 & \ddots & S_{16\,match+} \end{bmatrix} \quad [6\_2]$$

And $$S_{match+-} = \begin{bmatrix} S_{1\,match+-} & \ddots & 0 \\ \ddots & S_{n\,match+-} & \ddots \\ 0 & \ddots & S_{16\,match+-} \end{bmatrix}. \quad [6\_3]$$

Returning to equation 5, inserting Eq. 5 in Eq. 4 provides:

$$\begin{bmatrix} S_{drive\,drive} & S_{drive\,lump} \\ S_{lump\,drive} & S_{lump\,lump} \end{bmatrix} \begin{bmatrix} a_{drive} \\ a_{lump} \end{bmatrix} = \quad [7]$$

$$\begin{bmatrix} S_{match+}^{-1} \cdot a_{drive} \\ S_{lump}^{-1} \cdot a_{lump} \end{bmatrix} - \begin{bmatrix} S_{match+-} \cdot S_{match+}^{-1} \cdot a_{in} \\ 0 \end{bmatrix}.$$

To determine the array S-parameters from $b_{out}/a_{in}$, with $b_{out}$ given by the relationship between the matching circuits' $S_{match}$ parameters and $a_{drive}$, $b_{out}$ is expressed as:

$$b_{out} = S_{match+-} \cdot \frac{a_{drive} - S_{match+-} \cdot a_{in}}{S_{match+}} + S_{match-} \cdot a_{in}, \quad [8]$$

where $a_{drive}$ is calculated from Eq. 7 as $$S = \frac{b_{out}}{a_{in}} = S_{match+-} \cdot S_{match+}^{-1} \cdot \left( \frac{a_{drive}}{a_{in}} - S_{match+-} \right) + S_{match-}. \quad [10]$$

Thus the $\mathbb{C}^{16 \times 16}$ S-parameters of the array coil measured at the RF amplifier is expressed by:

$$S = b_{out}/a_{in} = S_{match+-} \cdot S_{match+}^{-1} \cdot (a_{drive}/a_{in} - S_{match+-}) + S_{match-}. \quad [10]$$

In the above 208-port array description, a lumped component description of the decoupling circuits was utilized. FIG. 1B shows the adjacent surface coils being decoupled using two types of decoupling circuits. Depending on the orientation, the nearest neighbor surface coils have mutual impedance $Z_{12} = -j\omega M_{12} + R_{12}$, where $\omega$ is coil resonant angular frequency $2\pi \times 298$ MHz. As shown in FIG. 1B, within a row (top or bottom), the horizontally adjacent coils are decoupled by RID circuits; the vertically and diagonally ("cornering") adjacent coils are decoupled by TD circuits (see FIG. 1D). For the RID circuit, both the reactive and resistive terms can be canceled when $\omega_0 < \omega$ while the TD eliminates the reactive term of the mutual impedance.

Referring back to Eq. 6, $S_{lump}$ is of $\mathbb{C}^{192 \times 192}$ and contains the S-parameters of lumped capacitors ($S_{cap}$) and decoupling circuits ($S_{DC}$), where $S_{DC}$ is of $\mathbb{C}^{80 \times 80}$ and contains the 40 decoupling circuits' S-parameters:

$$S_{DC} = \begin{bmatrix} S_{DC1} & \ddots & 0 \\ \ddots & S_{DCn} & \ddots \\ 0 & \ddots & S_{DC40} \end{bmatrix}, \quad [10\_1]$$

where $S_{DC\,n}$ is a $\mathbb{C}^{2 \times 2}$ S-parameters of the $n^{th}$ decoupling circuit. Since each decoupling circuit has 2 ports, we have:

$$S_{DCn} = \begin{bmatrix} S_{11} & S_{12} \\ S_{21} & S_{22} \end{bmatrix} = (Z_{DC\,n} - 50I)(Z_{DC\,n} + 50I)^{-1}, \quad [10\_2]$$

where the $Z_{Dc\,n}$ is a $\mathbb{C}^{2 \times 2}$ impedance matrix of the $n^{th}$ RID or TD circuit, and their expressions are calculated as below. As shown in FIG. 1B, the RID decoupling circuits are used to decouple within-row adjacent coil pairs, while the TD circuits are used to decouple "cornering" coils and between-row coil pairs. Using notations in FIG. 1D, The Z matrix ($\mathbb{C}^{2 \times 2}$) of each RID circuit expressed as:

$$Z_{RID} = \begin{bmatrix} j\omega L_0 + R_0 - \dfrac{\omega^2 k_0^2 L_0^2 \left( j\omega L_0 - \dfrac{j}{\omega C_0} + R_0 \right)}{\left( j\omega L_0 - \dfrac{j}{\omega C_0} + R_0 \right)^2 - \left( \dfrac{j}{\omega C_0} \right)^2} & \dfrac{-\omega^2 k_0^2 L_0^2 \left( \dfrac{j}{\omega C_0} \right)}{\left( j\omega L_0 - \dfrac{j}{\omega C_0} + R_0 \right)^2 - \left( \dfrac{j}{\omega C_0} \right)^2} \\ \dfrac{-\omega^2 k_0^2 L_0^2 \left( \dfrac{j}{\omega C_0} \right)}{\left( j\omega L_0 - \dfrac{j}{\omega C_0} + R_0 \right)^2 - \left( \dfrac{j}{\omega C_0} \right)^2} & j\omega L_0 + R_0 - \dfrac{\omega^2 k_0^2 L_0^2 \left( j\omega L_0 - \dfrac{j}{\omega C_0} + R_0 \right)}{\left( j\omega L - \dfrac{j}{\omega C_0} + R_0 \right)^2 - \left( \dfrac{j}{\omega C_0} \right)^2} \end{bmatrix}, \quad [10\_3]$$

where $$C_0 = \frac{2}{\omega_{02} L_0}, \text{ and}$$

$$R_0 = \omega_0 L_0 / Q_0.$$

To validate Eq. 10, the XFdtd-calculated $S_{CoilPorts}$ from Eq. 1 was converted to TOUCHSTONE file and imported into the N-port S-parameter instance in ADVANCED DESIGN SYSTEM (ADS 2020, KEYSIGHT, Santa Rosa, Calif.) and connected with corresponding circuit models (lumped capacitors, matching circuits, and decoupling circuits). The resulting S-parameters obtained at the 16 feed ports in the ADS 2020 N-port S-parameter instance are the same as the $\mathbb{C}^{16 \times 16}$ S-parameters obtained using Eq. 10.

The TD circuit Z matrix is written as:

$$Z_{TD} = \begin{bmatrix} j\omega L_1 + R_1 & j\omega k_1 L_1 \\ j\omega k_1 L_1 & j\omega L_1 + R_1 \end{bmatrix}, \quad [10\_4]$$

where $$R_1 = \omega L_1 / Q_1.$$

Thus, the Z matrix ($\mathbb{C}^{2\times 2}$) of each RID circuit is characterized by four variables $\omega_0$, $L_0$, $Q_0$ and $k_0$, representing the isolated resonant frequency, inductors, RID Q factor and coupling coefficients. Consequently, the capacitor value ($C_0$) and the inductor resistivity ($R_0$) can be determined based on $C_0 = 2/(\omega_0^2 L_0)$, and $R_0 = \omega_0 L_0 / Q_0$. The Z matrix ($\mathbb{C}^{2\times 2}$) of each TD circuit (see equation 10_4) is characterized by three variables $L_1$, $Q_1$ and $k_1$, representing inductors, inductor Q factor and the coupling coefficient. The inductor resistivity ($R_1$) of the TD circuit is given by $R_1 = \omega L_1 / Q_1$.

An optimization process is also disclosed herein. The optimization was performed using a cost function ($f(x)$) of a real number vector x of $\mathfrak{R}^{296}$ whose entries are coil parameters. The $f(x)$ is defined in Eq. 11, where $\|\ \|$ denotes the Euclidean distance, $|\ |$ is the elementwise absolute values, and $w_{1-3}$ are weights:

$$f(x) = w_1 \| |\text{diag}(S(x))| - S_{ii} \| + w_2 \| |S_r(x)| - S_{ij} \| + w_3 \left\| \frac{\text{Std}(B_1)}{\text{Mean}(B_1)} - \text{target} \right\|. \quad [11]$$

The minimum is given by the constrained optimization $$\hat{x} = \underset{x}{\arg\min}\{f(x)\}$$

over the 296 parameters, and each coil port has at least one parameter (see Table 1, left column for itemization for x), subject to $x \in \{\Omega: x_{n\ lower} < x_n < x_{n\ upper}, n=1, 2, \ldots, 296\}$.

Figure 3A:
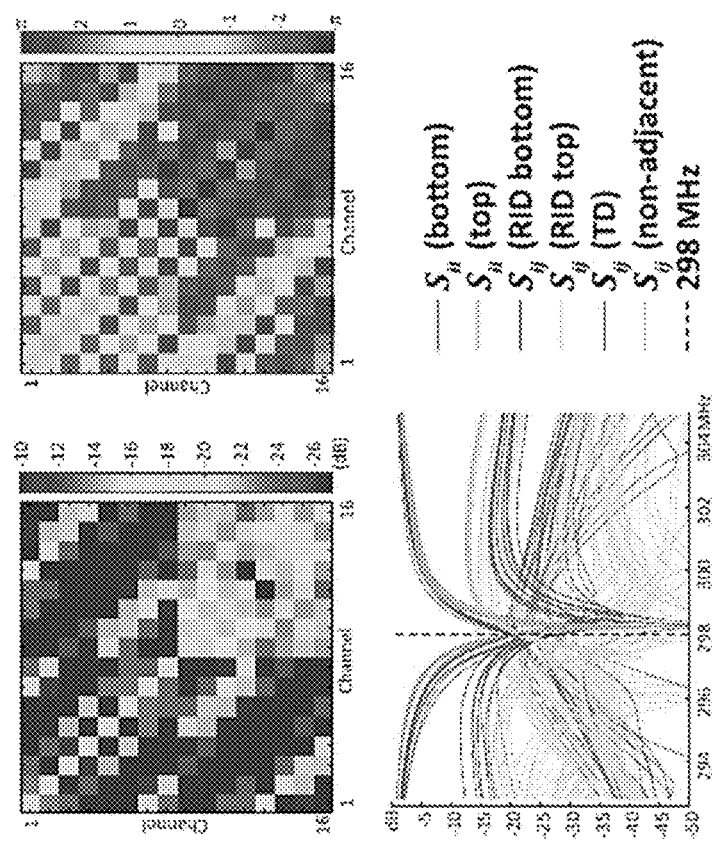
FIGS. 3A and 3B are magnitude (dB) and phase plots of the S-parameter matrix at 298 MHz, and frequency sweep determined from the cost function in Equation 11 (with $B_1^+$ homogeneity optimization) for the Louis model (as provided in FIG. 3A) and the equivalent data for Louis but determined with Equation 15, provided below, without $B_1^+$ homogeneity optimization (as provided in FIG. 3B).
Figure 3B:
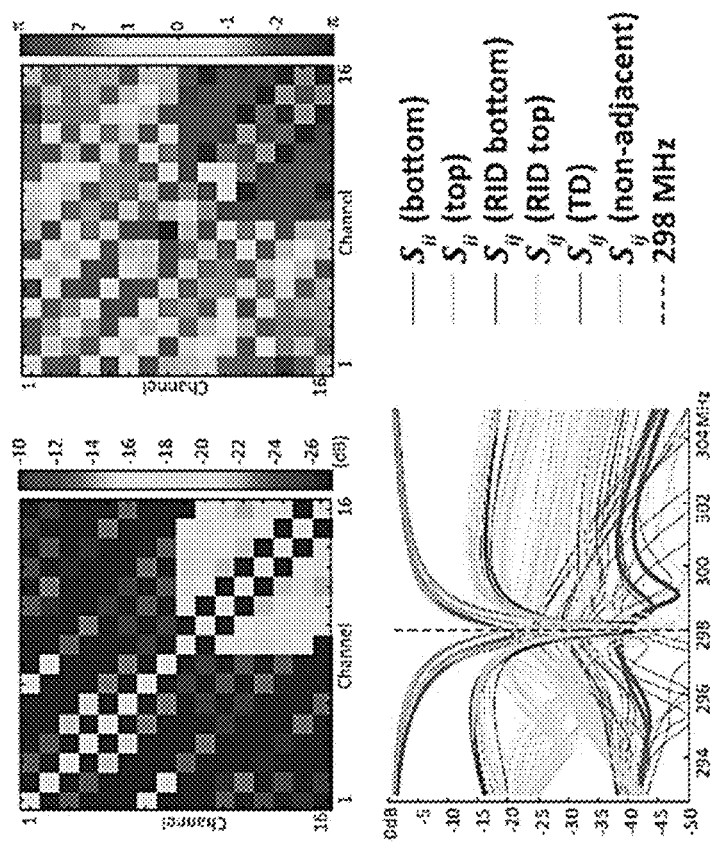

Eq. 11 contains three parts, with the first part optimizing the diagonal terms of the S-parameters $S(x)$ from Eq. 10 (denoted by $\text{diag}(S(x))$). The $S_{ii}$ is a column vector of $\mathbb{C}^{16\times 1}$, and its elements are set to a target value chosen from $-20$ to $-25$ dB (the best value is $-20$ dB). The second part is optimization of decoupling of any two adjacent coils, represented by the selected elements in the strictly lower triangle portion of the coil S-parameter (denoted by $S_r(x)$, terms are shown as $S_{ij(RID\ bot)}$, $S_{ij(RID\ top)}$, and $S_{ij(TD)}$ in FIGS. 3A and 3B frequency-sweep plots). FIGS. 3A and 3B are magnitude (dB) and phase plots of the S-parameter matrix at 298 MHz, and frequency sweep determined from the cost function in Equation 11 (with $B_1^+$ homogeneity optimization) for the Louis model (as provided in FIG. 3A) and the equivalent data for Louis but determined with Equation 15, without $B_1^+$ homogeneity optimization (as provided in FIG. 3B). The $S_{ij}$ is a column vector of $\mathbb{C}^{40\times 1}$, and its elements are set to a target value chosen from $-20$ to $-30$ dB (the best value is $-25$ dB); these boundary values are based on experimental data. Notably, $S_r(x)$ are effectively defined by the TD and RID circuits (rather than the sample), so the optimization of $S_r(x)$ is equivalent to optimization of the TD and RID circuits. The third part is the optimization of $B_1^+$ coefficient of variation (CV), a metric for $B_1^+$ homogeneity within the intracerebral tissue calculated using Eqs. 9, 12-14 (see below); we used a target $B_1^+$ CV of 10%. The weightings $w_1$, $w_2$ and $w_3$ were set at 0.1, 0.1, and 1.5, based on obtaining equal contributions to the $f(x)$ minimization from the three target parameters. To avoid large matrix sizes and to save optimization time, we downsampled the $B_1^+$ maps from $300^2$ to $64^2$ resolution over the 9 slices (i.e., $\sim 20$ fold reduction in matrix size) before calculating $\text{Std}(B_1^+)$ and $\text{Mean}(B_1^+)$.

This constrained optimization can be solved using algorithms such as Self Organizing Migrating Algorithm (SOMA), the alternating direction method of multipliers (ADMM) (the implementation is described in Appendix B), Genetic Algorithm (GA) and a nonlinear programming solver 'fmincon' using the 'interior-point' algorithm. Both GA and fmincon are provided in the MATLAB Optimization Toolbox (MathWorks, Natick, Mass.). The optimization performance of optimizing coil parameters in Eq. 11 are compared between the four algorithms (SOMA, GA, ADMM and 'fmincon'). We used fmincon as the optimization solver and searched for optimal x parameters within the upper and lower bounds.

As shown in Table 1, over the four modeled heads Ella, Duke, Hanako and Louis, the constrained optimization of $f(x)$ gave highly consistent values for all mean component values (264 parameters associated with the RID, TD, and distributed capacitors, excluding tuning and matching circuits). These values were thus used to define the "fixed" transceiver $T_0$. In the experiment, each coil in the array is tuned and matched on each subject. To mimic real-world workflow, $T_0$ was then used with optimization of the 32 tuning and matching capacitors ($x_{97}$ to $x_{128}$) for each head to estimate field maps and RF shim.

As shown in FIG. 2, the forward waves from the 8-channel RF amplifier are split to 16 forward waves ($a_{in}$) to feed the 16 coil elements. While the RF amplifier of the SIEMENS MAGNETOM 7T VB17 8 pTx system is capable of up to 165 V per channel, to target a final $B_1^+$ of 11.74 µT, each channel is optimized with a maximum of 110 V. To include the splitter and approximate real-world conditions, we applied 4.5 dB attenuation on the forward voltage, i.e., each coil received maximum 65.5 V forward voltage. Thus, the expression of forward voltage ($a_{in}$) for each coil at the coil plug-in is:

$$a_{in} = V_k e^{j(\phi_k)} = V_0 e^{j(\phi_{CP} + \Delta_{inter\text{-}row})}, \quad [12]$$

where $V_k$ is the forward voltage amplitude, and $\phi_k$ is applied forward voltage phase (k=1, 2, ..., 16). To generate a circularly polarized (CP) distribution, $\phi_{CP}$ is $\pi/4$ phase increments along the 8 channels in the azimuthal direction. It should be appreciated that there is an additional phase shift $\Delta_{inter\text{-}row}$ (identical for all 8 channels) between the top and bottom rows of the array, reflecting additional cable lengths associated with the splitter. An optimization of Eq. 11 over a range of $\Delta_{inter\text{-}row}$ (0-80°) showed the best $B_1^+$ homogeneity at $>50°$ (see FIG. 4B which is graph of $B_1^+$SD/Mean vs. inter-row $\Delta$ phase in degrees for inter-row coil element phase shifts from 0° to 80°). We used $\Delta_{inter\text{-}row} = 56°$ for the remainder of the work as presented herein.

The $a_{in}$ is a vector concatenating $a_{in}$ of all 16 coils. Substituting this $a_{in}$ into Eq. 9 gives $a_{drive}$, and using Eq. 13 gives $a_{lump}$.

$$a_{lump} = (S_{lump}^{-1} - S_{lump\ lump})^{-1} \cdot S_{lump\ drive} \cdot a_{drive} \quad [13]$$

After calculating $a_{drive}$ and $a_{lump}$, we can obtain the forward wave vector a in Eq. 2, and its elements $a_n$ are used in the following Eq. 14. Here we can use Eq. 14 to generate $B_1^+$ maps corresponding to the following driving conditions: (A) simultaneous transmission through all coils in CP-mode, using $a_{in}$ that has all elements equal to the voltages from Eq. 12; (B) single-coil transmission (16 channels), where each coil map is generated using $a_{in}$ that has only one element equal to the voltage value, and the rest being zeros; (C) pairwise transmission (8 channels), where each channel corresponds to a vertical pair of coils, generated using $a_{in}$ that contains two elements equal to the voltage value, and the rest being zeros. The 8-channel $B_1^+$ maps are later used to generate the optimized $B_1^+$ distribution.

$$B_1^+ = \sum_{n=1}^{208} a_n \cdot \frac{B_{1\,voltage\,source\,n}^+}{a_{voltage\,source\,n}} \quad [14]$$

where $a_n$ is the $n^{th}$ element of the forward wave vector a, the $B_{1\,voltage\,source\,n}^+$ is the $B_1^+$ field map generated by the $n^{th}$ voltage feed (one of the 208 voltage feeds in XFdtd), and $a_{voltage\,source\,n}$ is the forward voltage at the load of the $n^{th}$ voltage feed. The $a_{voltage\,source\,n}$ is calculated based on the load voltage and the reflection coefficient seen at the $n^{th}$ voltage. To check the accuracy of Eq. 14, a simplified coil array (without the decoupling and matching circuits) was used, i.e., a direct simulation was performed with XFdtd (although other FDTD software can be used) using 18.5 pF lumped capacitors and 1-volt voltage sources bridging the coil gaps. The resulting S-parameters and field maps are compared to the calculated co-simulated results obtained without decoupling and matching circuitry using Eqs. 10 and 14, respectively.

For the "Homogeneous" distribution that targets the intracerebral region, two Regions of interest (ROIs) are defined: an inner ROI ($ROI^{HomePhase}$) over which the phase per channel is calculated and a larger outer ROI ($ROI^{HomeAmp}$) that includes all of the intracerebral tissue. The mean phase in $ROI^{HomePhase}$ is subtracted from each channel's phase map to obtain a constant phase across all channels. The amplitudes of the forward voltages of the 8 channels are optimized to achieve the targeted $B_1^+$ (11.74 µT) in the $ROI^{HomeAmp}$.

The experimental procedure is next described. For each subject, each coil in the array was tuned and matched using an MRI compatible RF sweeper probe (MORRIS INSTRUMENTS INC., Ottawa CA). Due to the high degree of decoupling of the coils within the array, tuning and matching adjustments for individual coils were wholly independent, making the process non-iterative, achieved in 2-4 minutes (5-10 seconds per coil), with sufficient dynamic range to account for phantom and human head loading conditions.

The $B_1^+$ maps were acquired on SIEMENS MAGNETOM 7T VB17 8 pTx system using the vendor provided acquisition routines, which generate relative amplitude, phase and flip angle maps through: 1) a multi-slice gradient echo acquisition using a single transmit channel for each excitation and 2) a FLASH sequence with an initial preparatory weighting pulse delivered from a single channel. The $B_1^+$ maps were acquired with a FOV 240×240 mm$^2$, 64×64 resolution over 11 slices 5 mm thick/gap 5 mm. The $B_1^+$ data was acquired as part of the routine calibrations performed in an ongoing IRB approved study. n=10 subjects (6F), mean age 21.8+/-4.9.

Using the above described experimental procedures, the following results were obtained. Despite the variation in head sizes, the optimization yielded very consistent results as shown in Table 1, with an overall coil parameters CV of about 8%. Thus the "fixed" transceiver $T_0$ was defined from the mean values from the four heads for each component. Using $T_0$, we then optimized the tuning and matching capacitors to generate the coil S-parameter matrix at single frequency 298 MHz for each head model. The S-parameter matrices are shown in FIG. 3A, which have element-wise similar magnitude and phase over the four models. For all four models at 298 MHz, the $S_{ii}$ and $S_{ij}$ (for adjacent decoupled coil pairs) are close to their target values of −20 dB and −25 dB, respectively, while the $S_{ij}$ of the next adjacent coil (which is not explicitly decoupled) are all better than −14 dB. The top row 8 coils (the $9^{th}$ to $16^{th}$ coils) are more difficult to decouple because the top row coils are angled inward towards the human head, increasing the mutual resistance between adjacent coils. However, for all adjacent coils decoupled by the RID circuits, the S-parameter frequency sweep showed a dip, reaching $S_{ij}$ values of −30 dB to −50 dB.

Figure 4A:
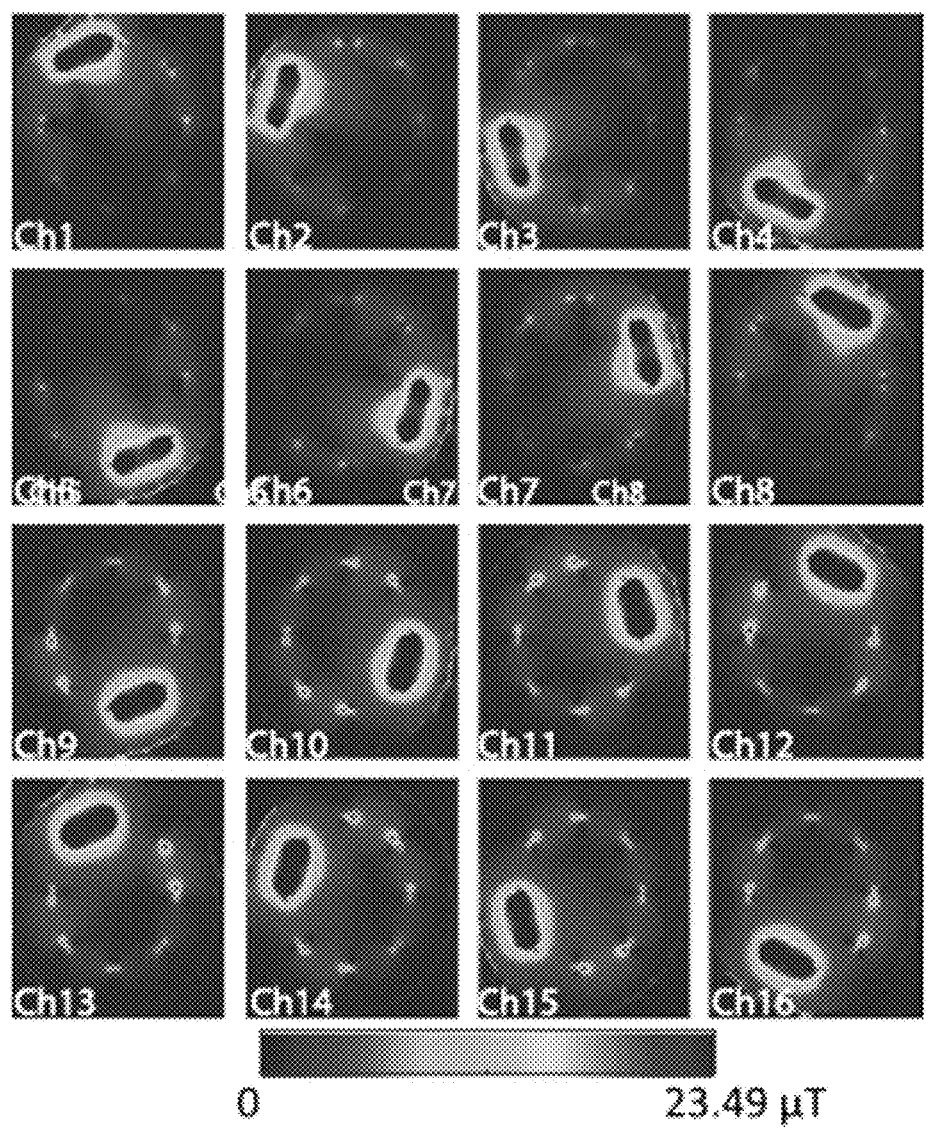
FIG. 4A provides the reconstructed $B_1^+$ magnitude profiles (reconstructed using Eq. 14, provided below) of all 16 coils loaded with the Louis model, and wherein each coil is fed with 65.5 V peak forward voltage.
Figure 4B:
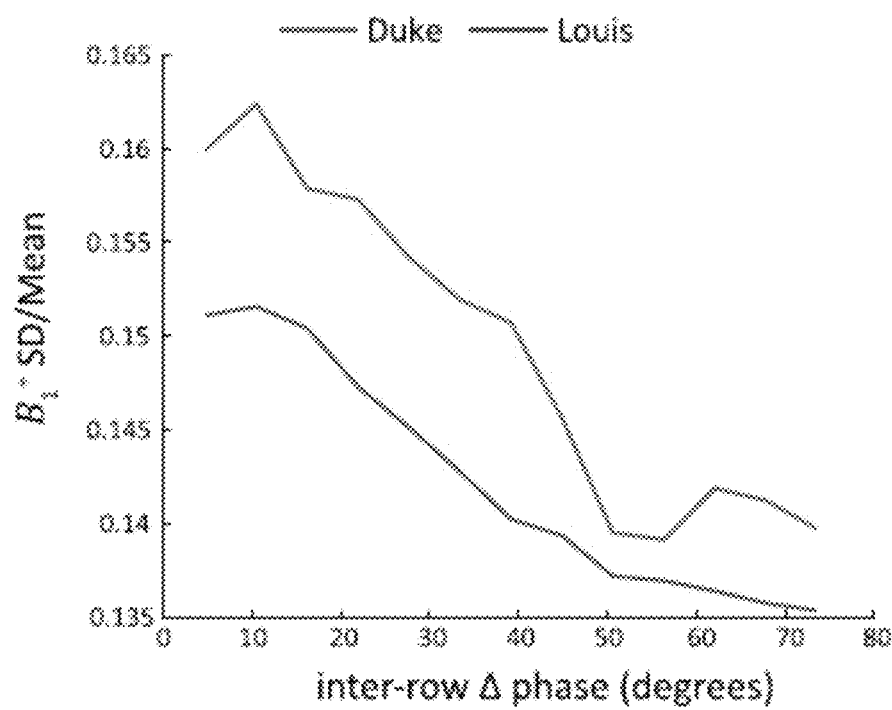
FIG. 4B is a graph of $B_1^+$SD/Mean vs. inter-row Δ phase in degrees for inter-row coil element phase shifts from 0° to 80°.

FIG. 4A shows the reconstructed $B_1^+$ magnitude profiles (reconstructed using Eq. 14) of all 16 coils loaded with the Louis model, and each coil is fed with 65.5 V peak forward voltage. Each coil has similar spatial distribution of $B_1^+$ magnitude, as each coil is well decoupled from the adjacent coils, with the coupling between the next nearest neighbor coils reaching −14 dB isolation (e.g., $S_{13,11}$ and $S_{14,12}$ in FIGS. 3A and 3B S matrix magnitude map). Allowing for variation in $\Delta_{inter-row}$, FIG. 4B shows that two simulating heads behaved similarly for resulting $B_1^+$ homogeneity variation, with an approximate minimum beyond >50.

Figure 5A:
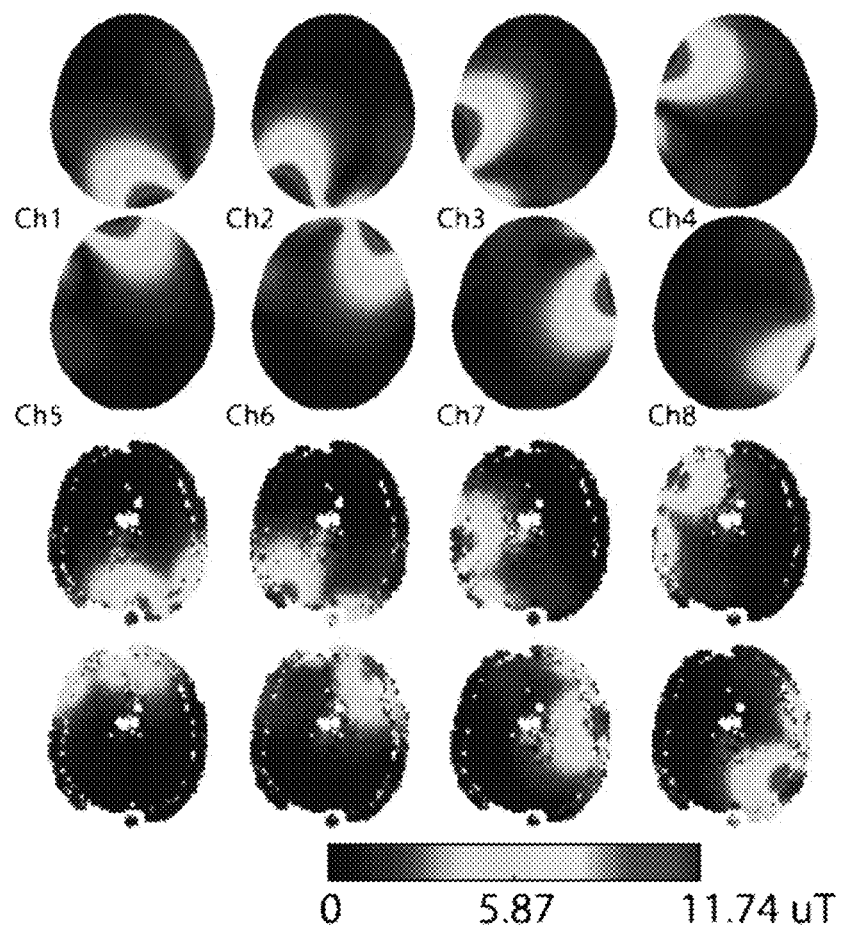
FIGS. 5A and 5B depict $B_1^+$ magnitude profiles of eight channels on one axial slice of the Louis model (first and second rows) and in vivo head (third and fourth rows) as provided in FIG. 5A; the $B_1^+$ phase profiles are presented in the same order as in FIG. 5A as shown in FIG. 5B.
Figure 5B:
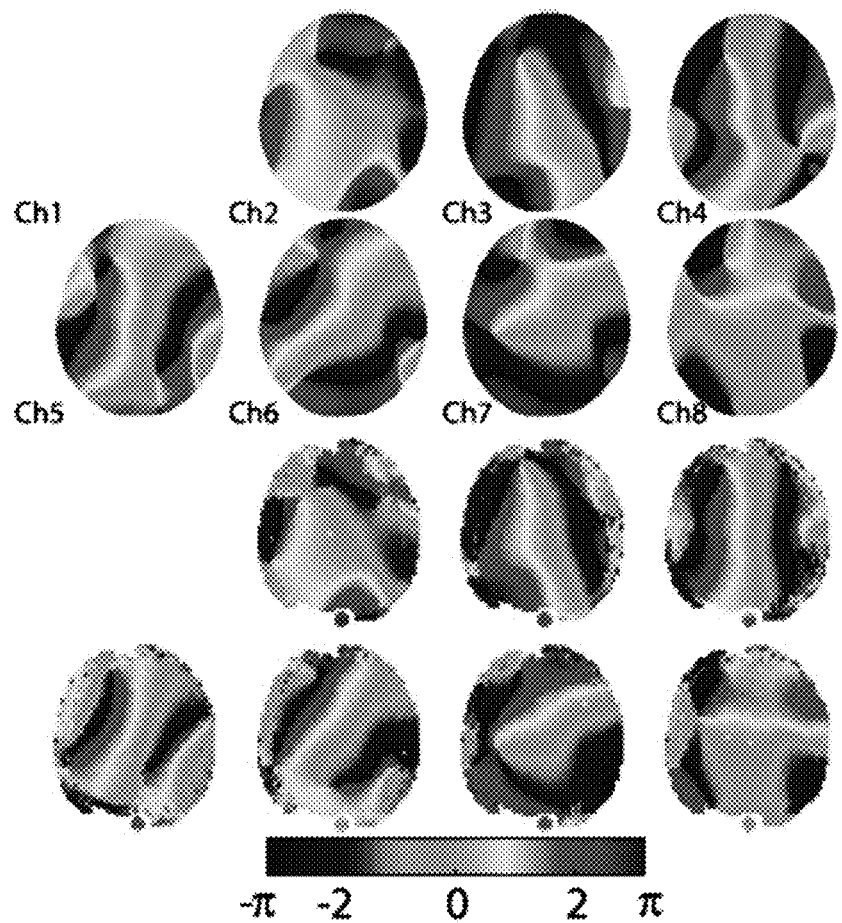
Figure 5D:
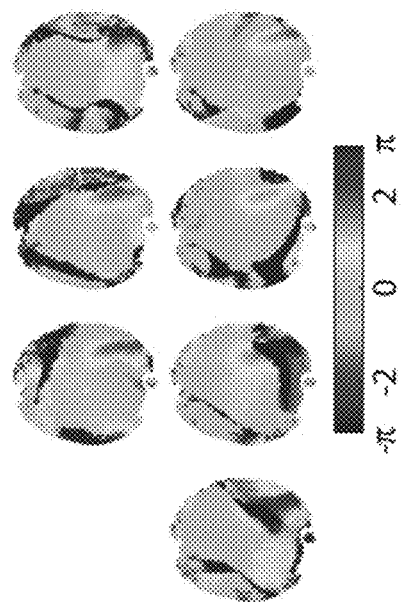
FIGS. 5C and 5D show absolute magnitude (FIG. 5C) and phase (FIG. 5D) of the profiles in FIGS. 5A and 5B.
Figure 5C:
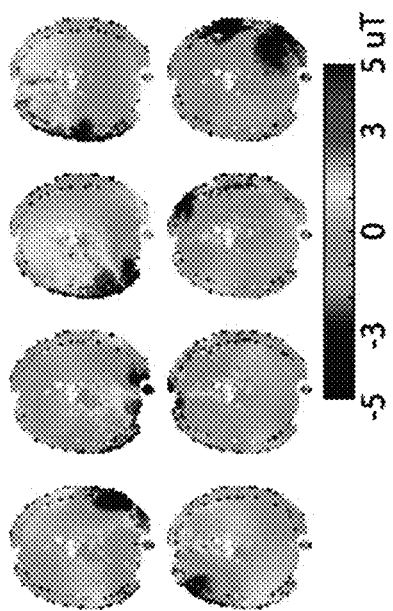

FIGS. 5A and 5B depict $B_1^+$ magnitude profiles of eight channels on one axial slice of the Louis model (first and second rows) and in vivo head (third and fourth rows) as provided in FIG. 5A; the $B_1^+$ phase profiles are presented in the same order as in FIG. 5A as shown in FIG. 5B. The phase map of each channel is relative to the first channel. In both the simulation and experiment, each coil element is fed with 65.5-V peak forward voltage. The absolute magnitude is shown in FIG. 5C and the phase is shown in FIG. 5D. FIGS. 5A-5D show difference between the Louis model and in vivo heads for each of the eight channels' $B_1^+$ profiles have good agreement in the $B_1^+$ maps (phase, amplitude) of individual channels between the Louis model and experimental data. In both simulation and experiment, each of the 16 coils is fed with 65.5 V peak forward voltage. Results from the RF shimmed homogeneous $B_1^+$ maps using cost function Eq. 11 are shown in FIGS. 6A and 6B and in Table 2, finding reasonable agreement with in vivo data obtained from eight human subjects.

Figure 6A:
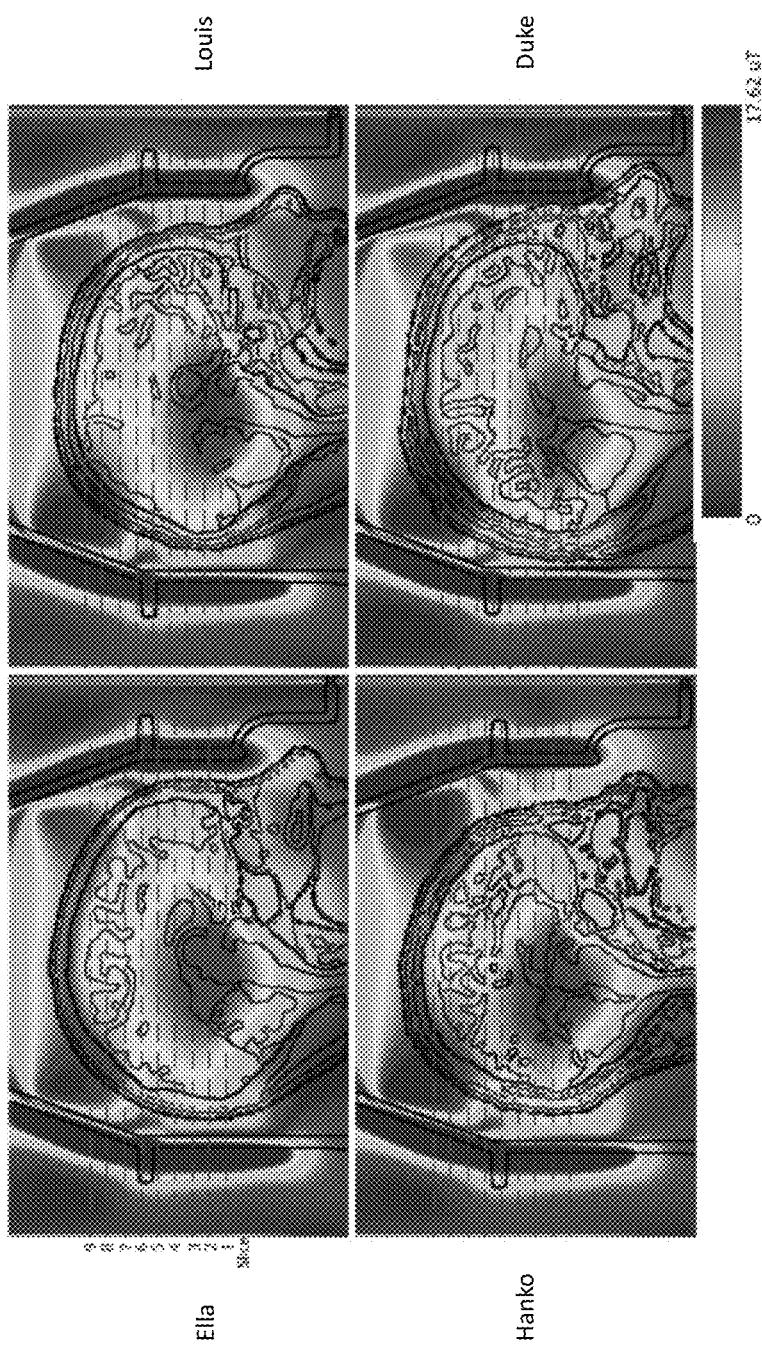
FIG. 6A shows Sagittal $B_1^+$ profiles of the RF-shimmed homogeneous distributions for the Ella (top left), Louis (top right), Hanako (bottom left), and Duke (bottom right) models.
Figure 6B:
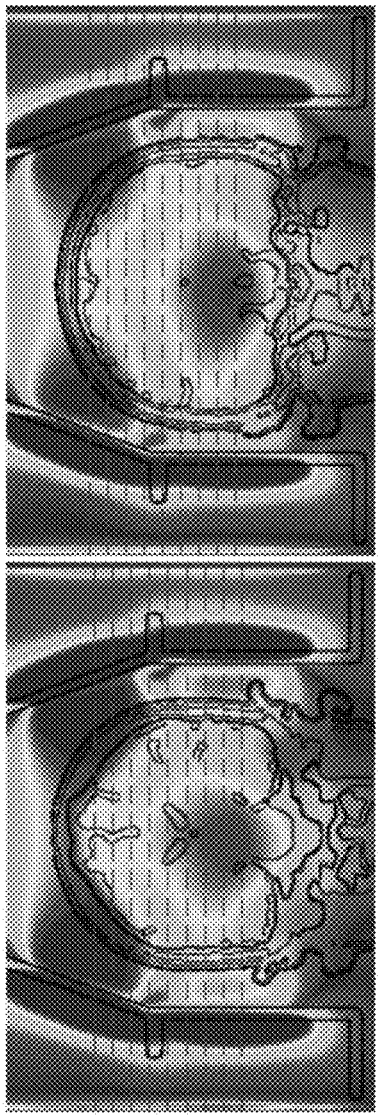
FIG. 6B provides the corresponding coronal $B_1^+$ profiles for the four head models shown in FIG. 6A.
Figure 6B:
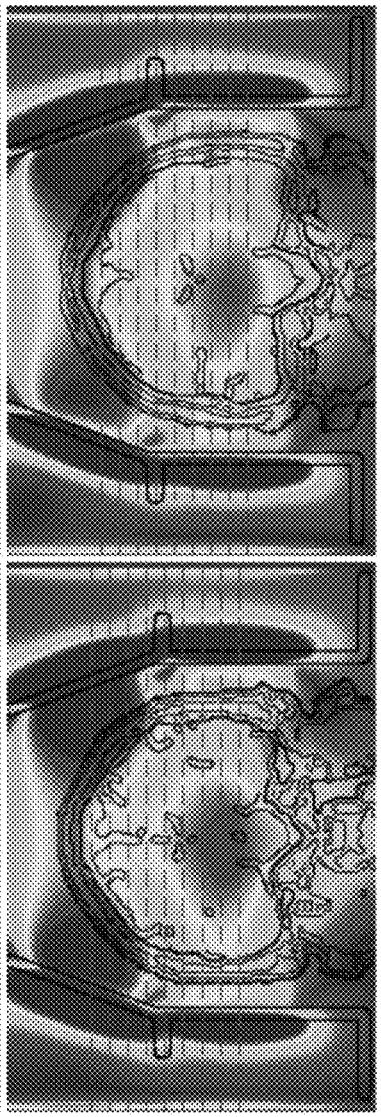
Figure 6B:
Figure 6B:
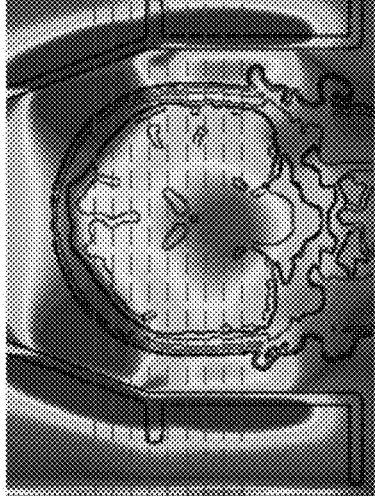
Figure 6B:
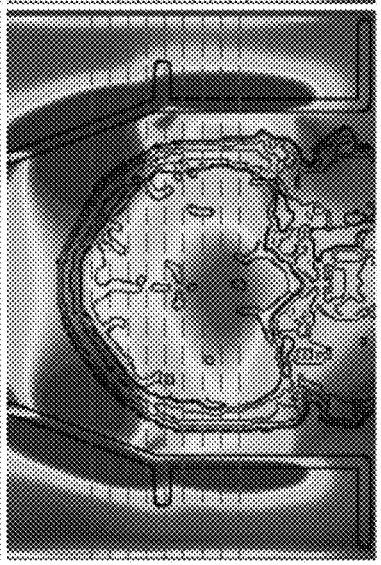

FIG. 6A shows Sagittal $B_1^+$ profiles of the RF-shimmed homogeneous distributions for the Ella (top left), Louis (top right), Hanako (bottom left), and Duke (bottom right) models. The nine region of interest slices indicated with dashed red lines are evenly spaced across the head. FIG. 6B provides the corresponding coronal $B_1^+$ profiles for the four head models.

Figure 7:
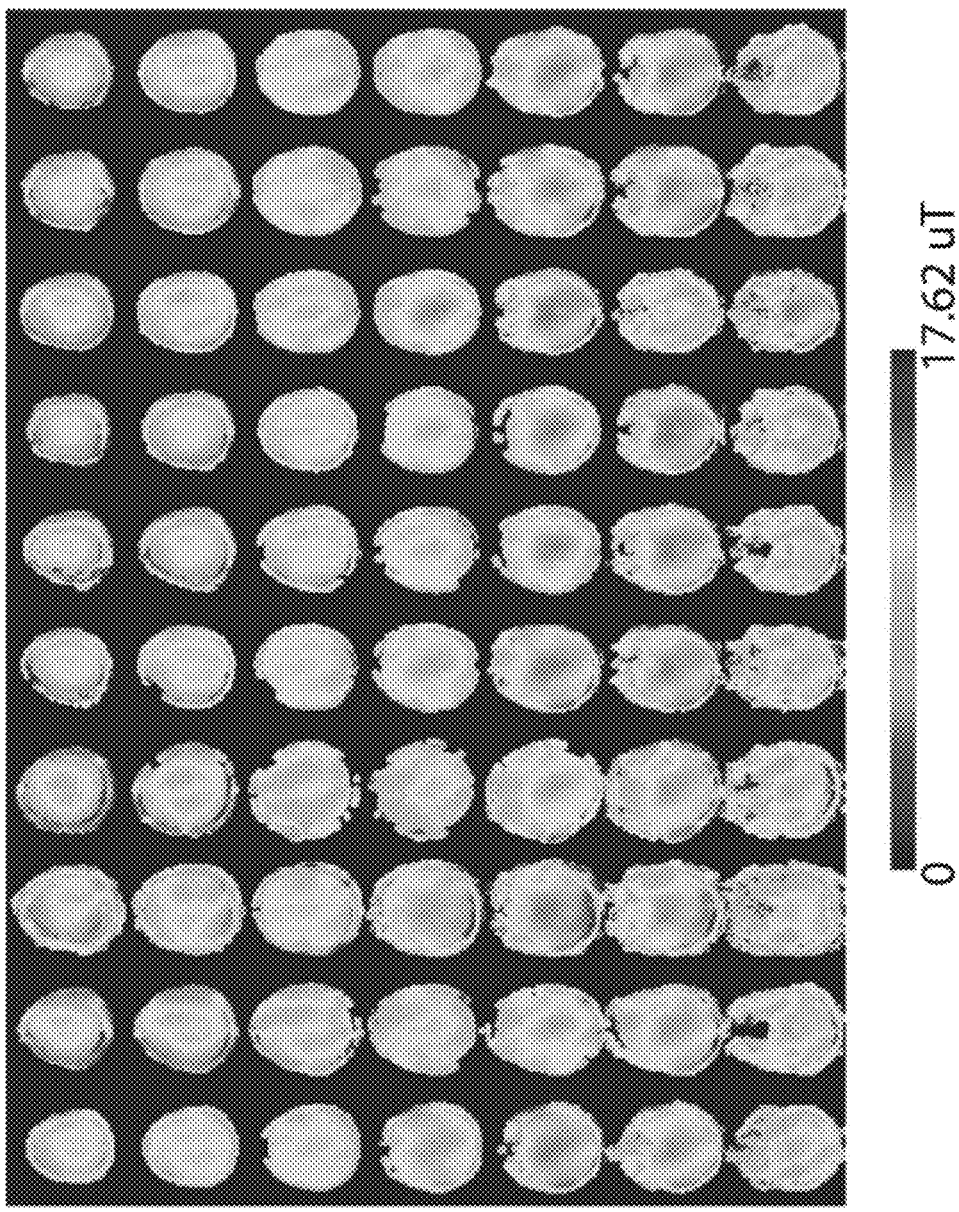
FIG. 7 provides RF-shimmed $B_1^+$ profiles from 10 volunteers. Each column includes seven evenly spaced axial slices from 1 volunteer.

FIG. 7 shows the RF-shimmed $B_1^+$ profiles from 10 volunteers. Each column includes seven evenly spaced axial slices from 1 volunteer.

Figure 8:
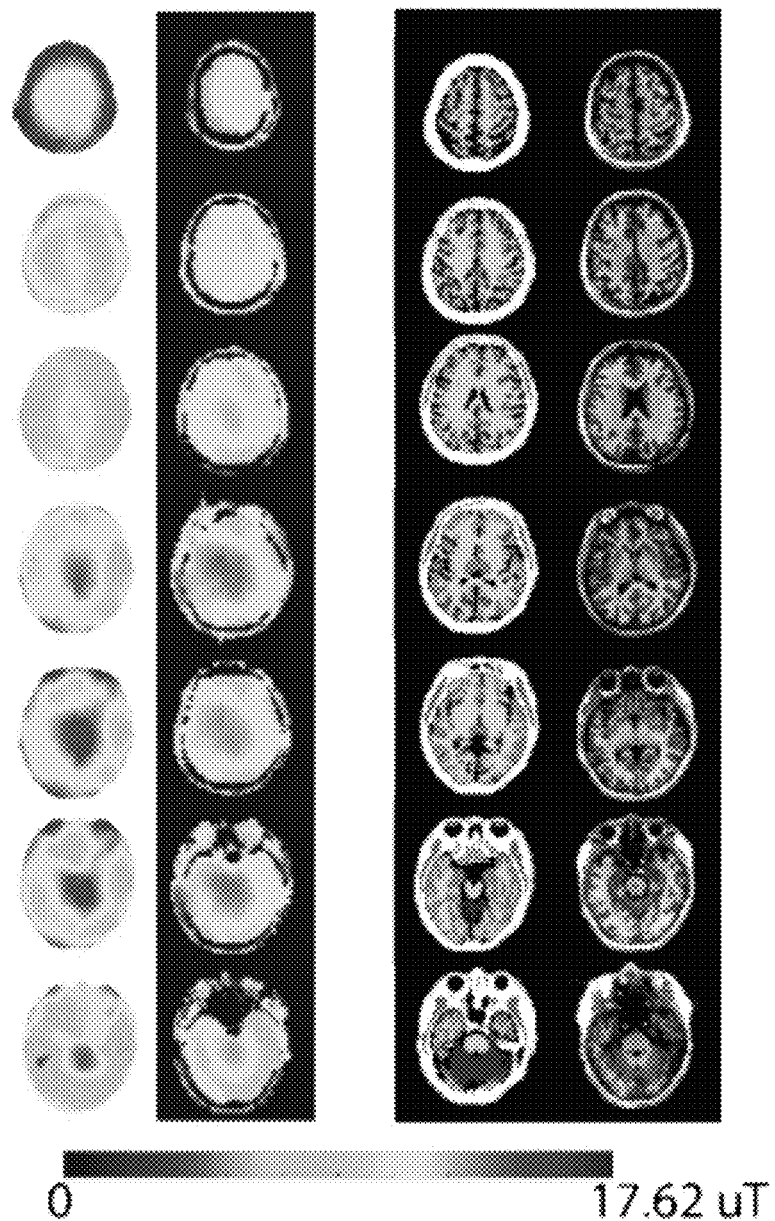
FIG. 8 shows a side-by-side comparison between simulation and in vivo $B_1^+$ maps of Hanako and a volunteer with similar head size.

FIG. 8 shows a side-by-side comparison between simulation and in vivo $B_1^+$ maps of Hanako and a volunteer with similar head size. Seven evenly spaced, RF-shimmed $B_1^+$ axial profiles of the Hanako model (first column) and in vivo heads (second column) are shown in FIG. 8; the corresponding tissue maps for the Hanako model and in vivo heads are shown in the third and fourth columns, respectively. There is excellent agreement in $B_1^+$ efficiency (mean $B_1^+$ in brain divided by forward power), achieving an in silico 11.16±0.35 µT/$\sqrt{W}$, in comparison in vivo 11.39 µT/$\sqrt{W}$, and good agreement in $B_1^+$ homogeneity, at 13.6±0.4% in silico, in comparison to our previous reports at 11-13% and 10.5±1.5% (n=8 subjects) in vivo.

TABLE 2

Mean and SDs of $B_1^+$ in the intracerebral tissue, and the total peak forward power of the RF amplifier for the homogeneous distribution

| | $B_1^+$ mean (µT) | $B_1^+$ SD (µT) | $B_1^+$ SD/mean % | Peak forward power (W) | $B_1^+$ efficiency (µT/√W) |
|---|---|---|---|---|---|
| A. With $B_1^+$ homogeneity in cost function | | | | | |
| Hanako (3.14 L) | 11.45 | 1.625 | 14.2 | 1920.8 | 0.2612 |
| Ella (3.20 L) | 11.47 | 1.564 | 13.6 | 1922.8 | 0.2616 |
| Duke (3.75 L) | 11.13 | 1.508 | 13.6 | 1936.0 | 0.2530 |
| Louis (3.28 L) | 11.53 | 1.508 | 13.1 | 1781.3 | 0.2732 |
| Mean simulated | 11.39 ± 0.18 | 1.550 ± 0.06 | 13.6 ± 0.4 | 1890.2 ± 72.9 | 0.2620 ± 0.0082 |
| In vivo (N = 8) | 11.10 ± 0.10 | 1.160 ± 0.17 | 10.5 ± 1.5 | 1723 ± 104 | 0.2675 |
| B, Excluding $B_1^+$ homogeneity in cost function | | | | | |
| Hanako | 11.16 | 2.208 | 19.8 | 1705.6 | 0.2701 |
| Ella | 11.17 | 1.895 | 17.0 | 1782.8 | 0.2645 |
| Duke | 11.11 | 1.914 | 17.2 | 1824.4 | 0.2600 |
| Louis | 11.34 | 1.832 | 16.2 | 1716.4 | 0.2736 |
| Mean simulated | 11.19 ± 0.10 | 1.964 ± 0.17 | 17.6 ± 1.6 | 1757.3 ± 56.3 | 0.2668 ± 0.0061 |
| C. Optimizing the user-tunable 32 tuning and matching capacitors on the fixed transceiver $T_0$ | | | | | |
| Hanako | 11.44 | 1.722 | 15.1 | 1846.1 | 0.2663 |
| Ella | 11.42 | 1.534 | 13.4 | 1931.0 | 0.2598 |
| Duke | 11.39 | 1.571 | 13.8 | 1915.7 | 0.2602 |
| Louis | 11.53 | 1.510 | 13.1 | 1748.2 | 0.2757 |
| Mean simulated | 11.45 ± 0.06 | 1.583 ± 0.09 | 13.8 ± 0.9 | 1860.3 ± 83.3 | 0.2656 ± 0.0075 |

Note:
The head volumes inside the RF shield are reported in the left column: including homogeneity weighting (Equation 11) (A). excluding homogeneity weighting (Equation 15) (B). perform the transceiver T optimization is performed individually over the four models, optimizing full set of parameter x in (A) and (B). The fixed transceiver $T_0$ is used in (C), as determined from the homogeneity weighted optimization.

Transceiver T optimization is performed individually over the four models, optimizing the full set of parameter x in (A) and (B). The fixed transceiver $T_0$ is used in (C), as determined from the homogeneity weighted optimization.

Table 2 shows the performance when using the $T_0$ transceiver on all four head models, optimizing only the tuning and matching capacitors. As expected, the $B_1^+$ efficiency and $B_1^+$ homogeneity are in good agreement with in vivo data.

The decoupled array design is advantageous due to better control of the coil interactions that affect homogeneity and amplitude. In this analysis, we were able to consider the homogeneity as a design feature in the cost function (Eq. 11) and examine the consequent impact on the coil components. For this comparison, we modified the cost function to eliminate the homogeneity condition, giving Eq. 15:

$$f(x) = w_1 \| \text{diag}(S(x)) | - S_{ii} \| + w_2 \| |S_r(x)| - S_{ij} \| \quad [15]$$

where the elements in $S_{ii}$ and $S_{ij}$ are set to –20 dB and –40 dB, respectively.

As shown in Table 2, comparing the effect of homogeneity weighting, the mean $B_1^+$ CV worsened by 28.4±7.5% to 17.5±1.6%, while the $B_1^+$ efficiency is slightly improved. Hanako exhibited the greatest change, an absolute 5% drop in CV, 14.2%>19.8%, i.e., a ~39% change in homogeneity. The consequences of omitting the homogeneity weighting for Hanako are seen throughout the decoupling circuits, with increased isolated RID resonance frequency and TD inductor values, decreased Q factors, RID inductor values, and RID k coefficients. FIGS. 3A and 3B compare the S-parameters and frequency sweeps calculated with and without homogeneity weighting for the Louis model. It is notable that with omission of the homogeneity weighting, the majority of change in the S-parameters amplitude and phase are in the top-top and top-bottom row coil interactions, with little effect in the bottom-bottom row interactions. Comparing with and without homogeneity weighting, the top-top and top-bottom $S_{ij}$ values are remarkably worse (larger values) with homogeneity weighting. Nonetheless, with homogeneity weighting, this range of values for the $S_{ij(RID\ top)}$, $S_{ij(RID\ bot)}$ and $S_{ij(TD)}$ is similar over the four models.

The present disclosure, thus, provides a co-simulation method, paired with S-parameters and $B_1^+$ homogeneity optimization to simulate a double-row, 16-coil head transmit array at 7 T. Our co-simulation model considered the matching circuits, decoupling circuits, and lumped capacitors. With the RID and TD circuits, the array coil can be tuned and matched at various loadings in silico with all coil elements achieving $S_{ij}$ coupling better than about –14 dB, consistent with known in vivo performance. The optimization parameters accurately characterized the decoupling circuits, e.g., the Q factors and isolated resonant frequencies of decoupling circuits are similar to those previously published, and would be important to account for the effect on RF power distribution by the decoupling circuits. Based on this co-simulation, the coil S-parameters and $B_1^+$ homogeneity can be optimized by different constrained optimization algorithms (ADMM, SOMA, GA, and fmincon). The resulting complex field maps of individual and summed coils show excellent agreement with in vivo data.

In the present disclosure a comparison of the behavior of the S-parameters using two cost functions that explicitly use spatial information (Eqs. 11 and 15) is provided. Comparing results with and without the homogeneity cost function, there were a significant 23% and 38% changes in the trimmer capacitor values on the matching circuit of top and bottom row coils respectively, and 21% change in the inductor values of the RID circuit on the bottom row coils. It is of interest that the homogeneity weighting worsens the $S_{ij}$ values, particularly affecting the top row coils and their coupling with the bottom row. This may reflect a penalty on power efficiency (1.9±1.5% decline, Table 2) in order to improve $B_1^+$ homogeneity. In this manner, the inclusion of the homogeneity cost function is effectively making use of both the magnitude and phase of the S-parameters, the phase which is commonly ignored in RF simulation studies.

Over the four heads placed in the coil center, the simulation generated highly consistent values for the component terms (Table 1). The head volumes inside the RF shield are reported in Table 2 left column. Several observations are of note. First, even though there is a 16.3% difference in head volume between the Duke head (3.75 liters, determined from all head tissue within the RF shield) and Hanako head (3.14 liters), there was no significant difference between any matching circuit or decoupling components and minimal differences in $S_{ij}$, indicating that with the applied decoupling circuits, the residual impedance is small. Second, the effects of the decoupling circuits are clear. As demonstrated by the validation simulation of Eq. 14, for a single activated coil at bottom row, the highest $S_{ij}$ about −8 dB) is with adjacent coil, significantly worse than the scenarios after adding the RIDs where the highest $S_{ij}$ about −15 dB) is with the next adjacent coils.

There is also good agreement between simulated and in vivo $B_1^+$ profiles and RF power efficiency. In RF shimming, we achieved a mean $B_1^+$ CV of 13.6±0.4% and $B_1^+$ efficiency 11.16±0.35 $\mu T/\sqrt{W}$ comparison to experimental data here of $B_1^+$ CV 10.5±1.5%, $B_1^+$ efficiency 11.37±0.26 $\mu T/\sqrt{W}$, and of 11-13% CV previously reported, Table 2. These residuals are the result of differences in head size and anatomical geometry which can affect the size of the intracerebral tissue ROIs and RF field propagation; for example, a less heterogeneous CSF distribution in brain result in less heterogeneous tissue conductivity and consequently less eddy current shielding. Residual differences can be a caused by head position or tilt within the array, or may still be affected by the accuracy of the model heads (e.g., in mesh size or tissue properties; for example, such measurements may depend on the temperature of the tissue, in vivo or in vitro.

Consequently, the improved correspondence of simulated and in vivo $B_1^+$ maps can reduce the model error for the array. A reduced model error will reduce the safety factor which is used to account for underestimation of the worst-case SAR. The present disclosure, thus, presents a hybrid circuit-spatial domain and cost function optimization to accelerate the FDTD simulation and design stages of a double row pTx head coil. The resulting field maps are in excellent agreement with in vivo results, and the high consistency of the coil components (typically varying by 2 to 8%, mean 3.4%) over the 4 simulated heads contends that the methods are robust and identify realistic component values. The inclusion of the spatial $B_1^+$ homogeneity into the cost function is novel and demonstrates that the optimization of this decoupled array is based on the desired homogeneity, amplitude, and power efficiency. The available solution space shows that a substantial gain in homogeneity (28%) can be achieved with a near-negligible (2%) loss in amplitude and efficiency. From a coil design view, the methods presented herein are not limited by the complexity of the coil designs such as the number of lumped components, nor coil-to-coil proximity, and should thus be applicable to analysis and simulation of array coil designs of higher port counts and geometrically overlaid coils. Therefore, no limitation should be applied to the specifics of the experimental procedures provided herein.

Figure 9A:
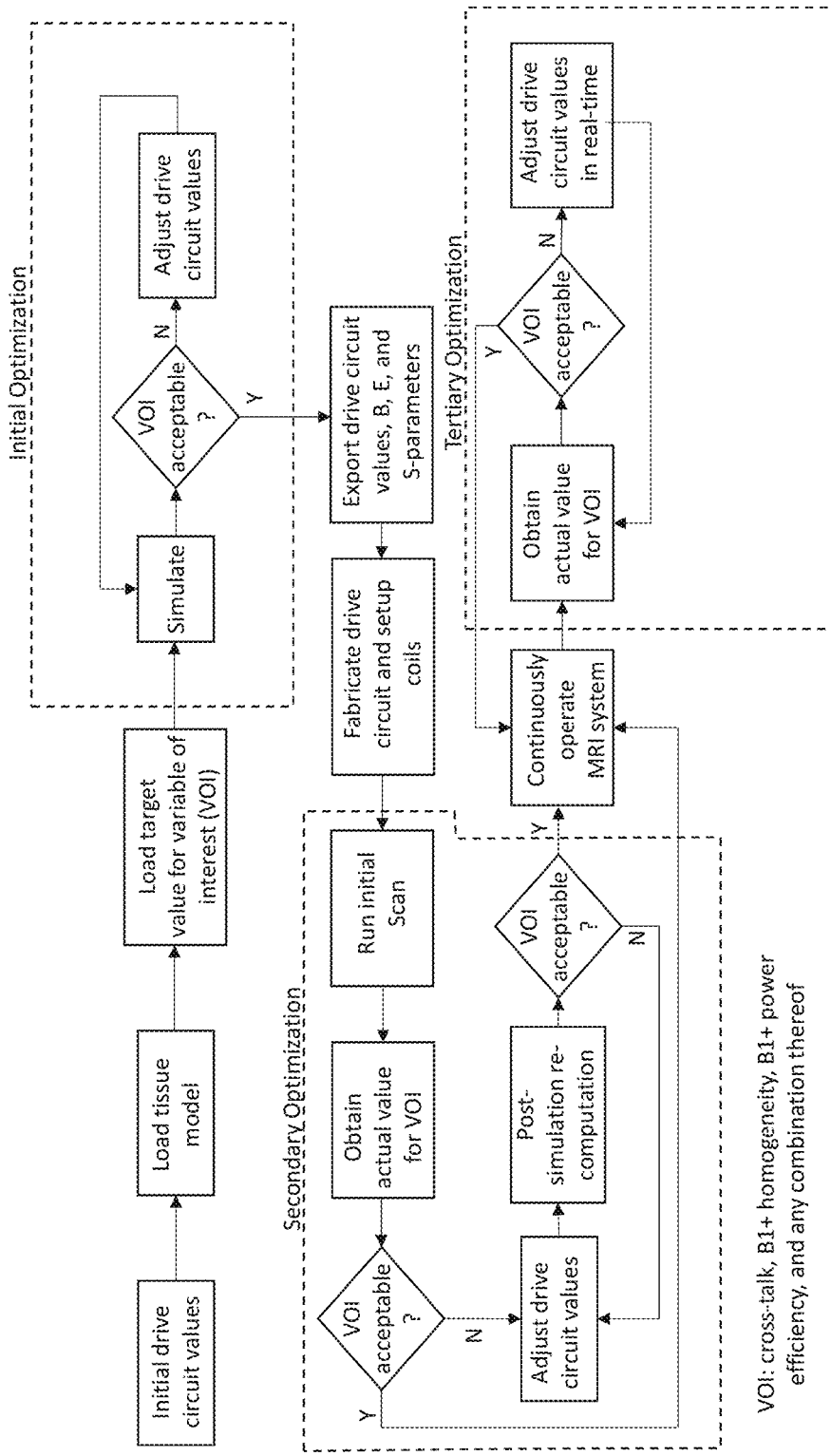
FIG. 9A is a block diagram describing steps performed by a controller (not shown) to carry out the method including simulation and optimization; and operation of the system of the present disclosure.

Referring to FIG. 9A, a block diagram is provided showing the multi-coil system and the method of operation of same of the present disclosure, according to one embodiment. Specifically, the block diagram shown in FIG. 9A describes steps performed by a controller (not shown) to carry out the method including simulation and optimization; and operation of the system of the present disclosure. A controller (not shown) begins with setting values for a drive circuit (initial values). Then the controller loads a tissue model as described above, followed by loading a target value for a variable of interest (VOI). The VOI can be any one of cross-talk, $B_1^+$ homogeneity, $B_1^+$ power efficiency, and any combination thereof. The controller (not shown) then optimizes based on a cost function (see Eq. 11). Iteratively, the controller (not shown) inquires whether the VOI has reached values within an acceptable range of the target. If not, then the drive circuit values are adjusted and the simulation is re-run. This iterative process constitutes the initial optimization, according to the present disclosure. A more detail representation of the simulation and optimization engine is presented in FIG. 9B, described below. Once the circuit parameters have been optimized for the VOI, the controller (not shown) exports circuit values, B, E, and S-parameters. These parameters are utilized to fabricate the drive circuit, and to setup the coils. Next, the controller (not shown) is used to run an initial scan of the tissue. The controller (not shown) obtains actual values of the VOI and determines if the actual values of VOI are within an acceptable initial range. If not, then the controller (not shown) iteratively adjusts circuit values and performs post-simulation and re-computation until the actual VOI are within the acceptable range. This iterative process constitutes a second optimization process. If, however, the controller (not shown) determines that the actual VOI values are acceptable, then it begins the scanning of the tissue in a continuous manner, immediately or after receiving input from a user. During the scanning of the tissue, the controller (not shown) continuously obtains actual VOI values and performs a third optimization by adjusting circuit values to maintain the actual VOI values within an acceptable operational range. This third optimization may be necessary if the subject moves or there is parametrical drift.

Figure 9B:
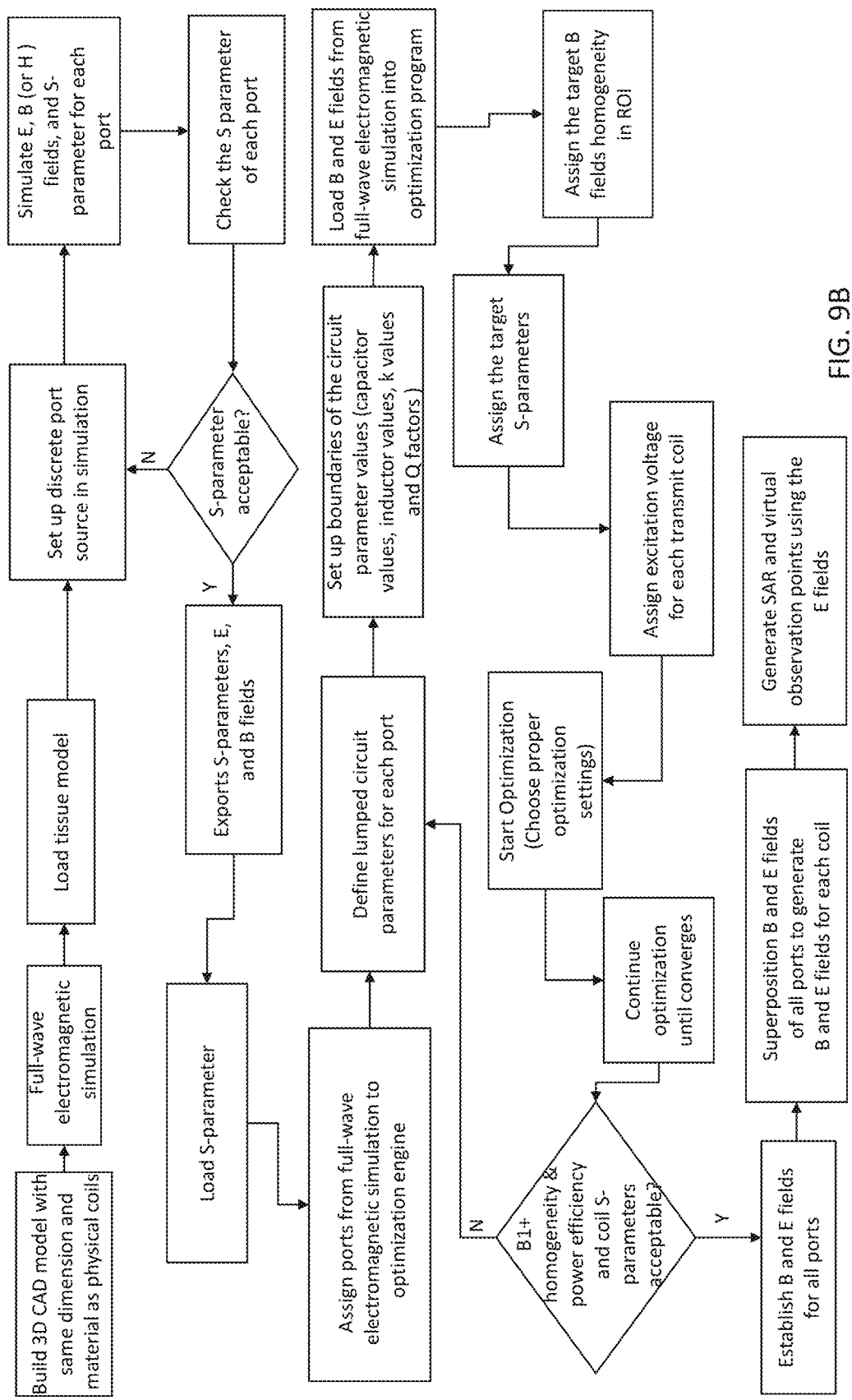
FIG. 9B is a block diagram that provides a more in-depth view of the simulation and optimization steps outlined in FIG. 9A.

Referring to FIG. 9B, the steps associated with simulation and the initial optimization are shown in more detail. The block diagram of FIG. 9B begins with the step of "Build 3D CAD model with same dimension and material as physical coils." This step is directed to coil computer aided design (CAD) models which refer to the 3D models of the coil, with the same material properties and dimension as the physical coil. The coil parameters include coil capacitor, inductor values and other circuit parameters known to a person having ordinary skill in the art. These parameters and models are thus loaded into a simulator (commercial simulators are available, as well as application specific simulators) in order to carry out a full-wave electromagnetic simulation. Next, a tissue model of a tissue of interest (human or animal), e.g., ELLA, LOUIS, HANAKO, or DUKE, is loaded into the simulator. Next, the discrete ports are setup by connecting the edges in the coil CAD model where the capacitor, inductor or power input are connected with voltage/current source, and where each source is associated with a corresponding port in the simulation. Next, the full-wave simulation is carried out to obtain magnetic field, associated electric field, and S-parameters for each port. Next, the S-parameter for each port is examined to determine if the S-parameter is within an acceptable range of benchtop measurements of the actual coil. If not, then the method of the present disclosure iteratively returns to the step of setting up discrete port and reruns the simulation. Once the S-parameters are within an acceptable range of benchtop measurements, then the method exports S-parameters, B and the associated E fields to an optimization engine. The optimization engine loads the S-parameters of each coil (simulated or actual), and assigns port parameters from the full-wave electromagnetic simulation. Next, the method defines the lumped circuit parameters for each port for the optimization engine. Next, boundaries for the lumped circuit parameters are defined based on a predefined set of boundaries. Next, the method loads B and associated E fields from the full-wave electromagnetic simulation software into optimization engine. Next, target S-parameter is provided to the optimization engine. Next, for the optimization engine excitation voltage for each transmit coil is assigned. Next, the optimization engine begins its optimization with optimization settings including choice of optimization solvers, optimization steps size, how many steps and initial values, as known to a person having ordinary skill in the art. The optimization engine continues its optimization until it converges to a solution which is when the cost function (see Eq. 11) reaches a stable value. It should be noted that in equation 11, the S-parameter (S) and B1 fields (B1) are all functions of x, and x is a vector of coil parameters such as capacitor values (C), inductor values (L) and decoupling circuit parameters such as coupling coefficient (k) and quality factor (Q). In the optimization, the method of the present disclosure is optimizing x with a choice of step size of delta x. After, e.g., 10000 steps, the cost function $f(x)$ becomes a stable value, at which point the optimization is considered as having converged. Furthermore, it should be noted that in equation 11, Sii, Sij are given by the users as the target S parameters. And the "target" in equation 11 is the B1 homogeneity (or B1 coefficient of variation) as a target value given by the user (i.e., VOI). Once the cost function $f(x)$ is stable, the diag(S(x)) should be close to $S_{ii}$, $S_r(x)$ should be close to $S_{ij}$ and Std(B1(x))/Mean(B1(x)) should be close to the target $B_1^+$ homogeneity. Next, different VOIs (cross-talk, $B_1^+$ homogeneity, $B_1^+$ power efficiency, and any combination thereof) are tested to determine if within an acceptable range of an associated target. If no, then the method moves back to the step of lumped circuit parameters and readjusting those. If yes, then the method moves the established B and the associated E field for all the ports, and proceeds to superposition B and E fields of all ports to generate B and E fields for each coil. Next the method generates specific absorption rate (SAR) prediction for region of interest (as previously identified ROI) as well as virtual observation points using the E-fields.

Figure 10:
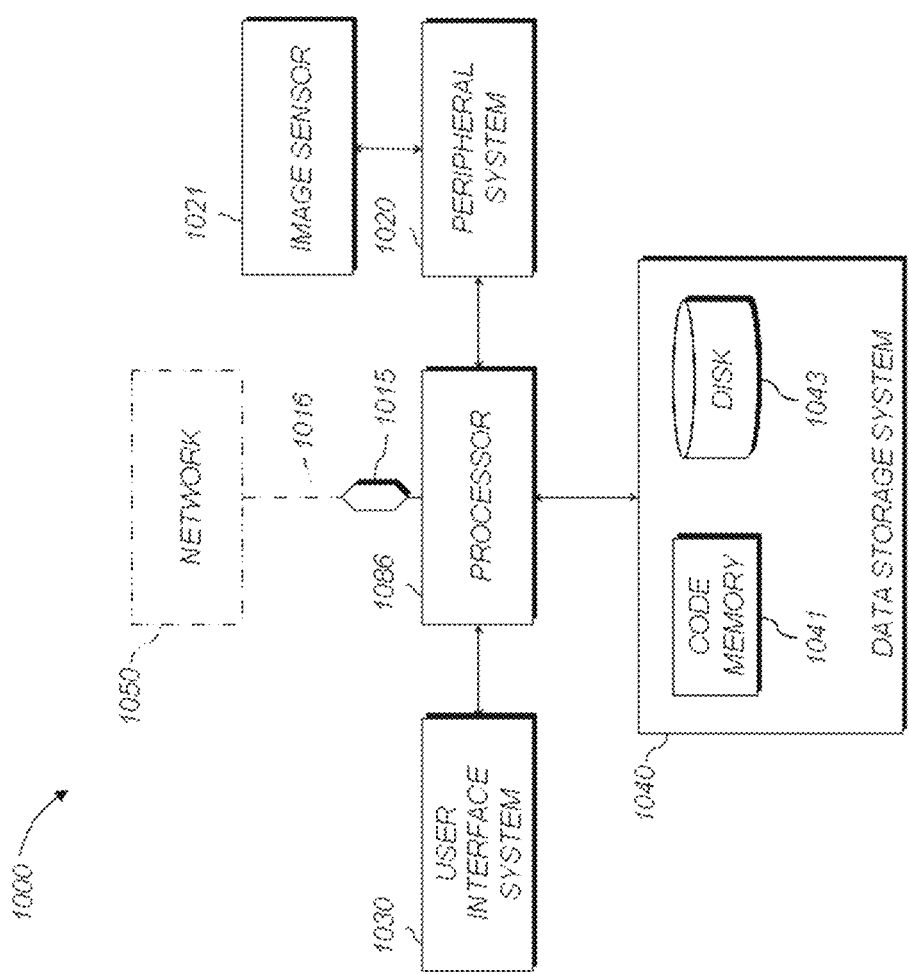
FIG. 10 is an example of a computer system constituting the controller (not shown) of FIG. 9A that can carry out the steps of the system of the present disclosure.

Referring to FIG. 10, an example of a computer system that constitutes the controller (not shown) discussed with reference to FIG. 9A is provided that can interface with the above-discussed MRI system. Referring to FIG. 6, a high-level diagram showing the components of an exemplary data-processing system 1000 for analyzing data and performing other analyses described herein, and related components. The system includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The imaging described in the present disclosure may be obtained using imaging sensors 1021 and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 1086 can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 1086 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (connected, e.g., via a network or a null-modem cable), or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable storage medium to which it is connected. The server can retrieve the code from the medium and transmit it through network 1050 to communication interface 1015.

The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects. These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors), to cause functions, acts, or operational steps of various aspects herein to be performed by the processor 1086 (or other processors). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

It should be noted that while the present disclosure make references to transceivers, implying a coil array that performs both transmit and receive, coil arrays that are configured to only perform transmit, as well as transmit arrays are within the ambit of the present disclosure.

Those having ordinary skill in the art will recognize that numerous modifications can be made to the specific implementations described above. The implementations should not be limited to the particular limitations described. Other implementations may be possible.

The invention claimed is:

1. A method of operating a multi-coil magnetic resonance imaging system, comprising:
   establishing initial circuit values of a drive circuit;
   a controller having a processor and software loaded on tangible memory loading a tissue model associated with a tissue to be imaged;
   the controller loading target values for a variable of interest (VOI) associated with operation of two or more coils of a magnetic resonance imaging system;
   the controller performing a simulation based on the established circuit values and the loaded tissue model;
   the controller determining output values of the VOI based on the simulation;
   the controller comparing the simulated output values of the VOI to the loaded target values of the VOI;
   if the simulated output values are outside of a predetermined envelope about the loaded target values of the VOI, then the controller performing a first optimization, wherein the first optimization includes:
   establishing a cost function based on the VOI, and
   iteratively minimizing the cost function by iteratively adjusting the circuit values until the cost function changes between iterations is less than a predetermined threshold,
   re-simulating, and
   re-comparing the simulated output values of the VOI to the loaded target values of the VOI until the simulated output values are within the predetermined envelope thereby establishing VOI optimized values; and
   loading the established VOI optimized values and operating the magnetic resonance imaging system on the tissue to be imaged.

2. The method of claim 1, wherein the cost function is defined as:

$$f(x) = w_1 \| |\text{diag}(S(x))| - S_{ii} \| + w_2 \| |S_r(x)| - S_{ij} \| + w_3 \left\| \frac{Std(B_1)}{Mean(B_1)} - \text{target} \right\|.$$

wherein
   $f(x)$ is the cost function of a real number vector x whose entries are coil parameters,
   $\| \ \|$ denotes the Euclidean distance,
   $| \ |$ is the elementwise absolute values,
   $w_{1-3}$ are weights,
   $B_1^+$ represents field associated with each coil of the two or more coils, and target represents target values for the variable of interest.

3. The method of claim 2, wherein the VOI is cross-talk between any two neighboring coils.

4. The method of claim 2, wherein VOI is $B_1^+$ homogeneity.

5. The method of claim 2, wherein VOI is $B_1^+$ power efficiency.

6. The method of claim 2, wherein VOI is a combination of cross-talk between any two neighboring coils and $B_1^+$ homogeneity.

7. The method of claim 2, further comprising:
exporting one or more of the circuit values, magnetic and electric field values as well as S-parameters of each of the two or more coils;
performing an initial scan of a tissue of interest associated with the tissue model;
obtaining actual output values of the VOI;
if the actual output values of the VOI of the initial scan are outside of a predetermined envelope about the loaded target values of the VOI, then performing a second optimization, wherein the second optimization includes:
establishing an error parameter based on the actual measured VOI from the initial scan vs. the loaded target values, and
iteratively adjusting the circuit values using a first gradient descent optimization process,
re-computing the VOI, and
re-comparing the recomputed values of the VOI to the loaded target values of the VOI until the recomputed VOI values are within the predetermined envelope about the loaded target values of the VOI.

8. The method of claim 7, wherein the VOI is one of cross-talk, $B_1^+$ homogeneity, $B_1^+$ power efficiency, and any combination thereof.

9. The method of claim 7, further comprising:
exporting one or more of the post circuit values, magnetic and electric field values as well as S-parameter of each of the two or more coils;
continuously operating the two or more coil;
obtaining continuous actual output values of the VOI;
if the continuous actual output values of the VOI are outside of a predetermined operational envelope about the loaded target values of the VOI, then performing a third optimization, wherein the third optimization includes:
iteratively adjusting the circuit values using a second gradient descent optimization process,
continuously operating the two or more coils, and
re-comparing the actual output values of the VOI to the loaded target values of the VOI until the actual output values are within the predetermined operational envelope.

10. The method of claim 9, wherein the VOI is one of cross-talk, $B_1^+$ homogeneity, $B_1^+$ power efficiency, and any combination thereof.

11. A drive system for a multi-coil magnetic resonance imaging system, comprising:
two or more coils utilized for imaging a tissue of interest;
a drive circuit for driving the two or more coils;
a controller having a processor and software loaded on tangible memory adapted to perform:
establish initial circuit values of a drive circuit;
load a tissue model associated with a tissue to be imaged;
load target values for a variable of interest (VOI) associated with operation of two or more coils of a magnetic resonance imaging system;
perform a simulation based on the established circuit values and the loaded tissue model;
determine output values of the VOI based on the simulation;
compare the simulated output values of the VOI to the loaded target values of the VOI;
if the simulated output values are outside of a predetermined envelope about the loaded target values of the VOI, then perform a first optimization, wherein the first optimization includes:
establish a cost function based on the VOI, and
iteratively adjust the cost function by iteratively adjusting the circuit values until the cost function changes between iterations is less than a predetermined threshold,
re-simulating,
re-compare the simulated output values of the VOI to the loaded target values of the VOI until the simulated output values are within the predetermined envelope, thereby establishing VOI optimized values; and
load the established VOI optimized values in order to operate the magnetic resonance imaging system on the tissue to be imaged.

12. The system of claim 11, wherein the cost function is defined as:

$$f(x) = w_1 \| |\text{diag}(S(x))| - S_{ii} \| + w_2 \| |S_r(x)| - S_{ij} \| + w_3 \left\| \frac{Std(B_1)}{Mean(B_1)} - \text{target} \right\|.$$

wherein
$f(x)$ is the cost function of a real number vector x whose entries are coil parameters,
$\| \ \|$ denotes the Euclidean distance,
$| \ |$ is the elementwise absolute values,
$w_{1-3}$ are weights,
$B_1^+$ represents field associated with each coil of the two or more coils, and target represents target values for the variable of interest.

13. The system of claim 12, wherein the VOI is cross-talk between any two neighboring coils.

14. The system of claim 12, wherein VOI is $B_1^+$ homogeneity.

15. The system of claim 12, wherein VOI is $B_1^+$ power efficiency.

16. The system of claim 12, wherein VOI is a combination of cross-talk between any two neighboring coils and $B_1^+$ homogeneity.

17. The system of claim 12, the controller further adapted to:
export one or more of the circuit values, magnetic and electric field values as well as S-parameter of each of the two or more coils;
perform an initial scan of a tissue of interest associated with the tissue model;
obtain actual output values of the VOI;
if the actual output values of the VOI of the initial scan are outside of a predetermined envelope about the loaded target values of the VOI, then performing a second optimization, wherein the second optimization includes:
establish an error parameter based on the actual measured VOI from the initial scan vs. the loaded target values, and
iteratively adjust the circuit values using a first gradient descent optimization process,
re-compute the VOI, and
re-compare the recomputed values of the VOI to the loaded target values of the VOI until the recomputed VOI values are within the predetermined envelope about the loaded target values of the VOI.

18. The system of claim 17, wherein the VOI is one of cross-talk, $B_1^+$ homogeneity, $B_1^+$ power efficiency, and any combination thereof.

19. The system of claim 17, the controller further adapted to:
- export one or more of the post circuit values, magnetic and electric field values as well as S-parameter of each of the two or more coils;
- continuously operate the two or more coil;
- obtain continuous actual output values of the VOI;
- if the continuous actual output values of the VOI are outside of a predetermined operational envelope about the loaded target values of the VOI, then performing a third optimization, wherein the third optimization includes:
  - iteratively adjust the circuit values using a second gradient descent optimization process,
  - continuously operate the two or more coils, and
  - re-compare the actual output values of the VOI to the loaded target values of the VOI until the actual output values are within the predetermined operational envelope.

20. The system of claim 19, wherein the VOI is one of cross-talk, $B_1^+$ homogeneity, $B_1^+$ power efficiency, and any combination thereof.

* * * * *